US012419550B2

(12) United States Patent
Zand et al.

(10) Patent No.: US 12,419,550 B2
(45) Date of Patent: Sep. 23, 2025

(54) APPARATUS, SYSTEMS, AND METHODS FOR MAPPING OF TISSUE OXYGENATION

(71) Applicant: SURGISENSE CORPORATION, Bethesda, MD (US)

(72) Inventors: Jason Matthew Zand, Washington, DC (US); Gregory Scott Fischer, Jamaica Plain, MA (US); Justin Thomas Knowles, Fairfax, VA (US)

(73) Assignee: SURGISENSE CORPORATION, Bethesda, MD (US)

( * ) Notice: Subject to any disclaimer, the term of this patent is extended or adjusted under 35 U.S.C. 154(b) by 446 days.

(21) Appl. No.: 17/507,015

(22) Filed: Oct. 21, 2021

(65) Prior Publication Data

US 2022/0287603 A1 Sep. 15, 2022

Related U.S. Application Data

(63) Continuation of application No. 16/165,222, filed on Oct. 19, 2018, now abandoned, which is a
(Continued)

(51) Int. Cl.
*A61B 5/00* (2006.01)
*A61B 1/00* (2006.01)
(Continued)

(52) U.S. Cl.
CPC ........ *A61B 5/14556* (2013.01); *A61B 1/0005* (2013.01); *A61B 1/005* (2013.01);
(Continued)

(58) Field of Classification Search
CPC . A61B 5/14556; A61B 5/0035; A61B 5/0071; A61B 5/0084; A61B 5/015;
(Continued)

(56) References Cited

U.S. PATENT DOCUMENTS

| 4,476,870 A | 10/1984 | Peterson et al. |
| 4,515,165 A | 5/1985 | Carroll |

(Continued)

FOREIGN PATENT DOCUMENTS

| CN | 1150749 A | 5/1997 |
| CN | 1969773 A | 5/2007 |

(Continued)

OTHER PUBLICATIONS

Hassan et al. "Fluorescence Lifetime Imaging System for In Vivo Studies," NIH Public Access; Mol. Imaging, 2007; 6 (4): 229-236.
(Continued)

*Primary Examiner* — Khai M Nguyen
(74) *Attorney, Agent, or Firm* — Michele V. Frank; Venable LLP

(57) ABSTRACT

Apparatus, systems, and methods are provided that generate in vivo maps of oxygenation measurements of biological tissue. These may include surgical instruments and stand-alone imaging systems with incorporated oxygen sensing capability. Oxygenation maps can be determined via fluorescent or phosphorescent lifetime imaging of an injectable probe with an oxygen-dependent optical response. Probe configuration and methods and apparatus of injecting the probe into the tissue are provided. Methods and apparatus for temperature compensation of temperature-dependent lifetime measurements are provided to improve oxygenation measurement accuracy. Oxygen maps may be registered with visible light images to assist in assessing tissue viability or localize anomalies in the tissue. Resulting oxygen images may be used for various applications including, but not limited to, guiding surgical procedures such as colorectal resection through use of intraoperative sensing, enhanced endoscopic imaging for identifying suspect lesions during
(Continued)

colonoscopy, and external imaging of tissue such as assessing peripheral vascular disease.

12 Claims, 24 Drawing Sheets

Related U.S. Application Data continuation of application No. 14/679,707, filed on Apr. 6, 2015, now abandoned.

(60) Provisional application No. 62/061,079, filed on Oct. 7, 2014, provisional application No. 61/975,742, filed on Apr. 5, 2014.

(51) Int. Cl.

| | | |
|---|---|---|
| *A61B 1/005* | (2006.01) | |
| *A61B 1/012* | (2006.01) | |
| *A61B 1/018* | (2006.01) | |
| *A61B 1/04* | (2006.01) | |
| *A61B 1/06* | (2006.01) | |
| *A61B 5/01* | (2006.01) | |
| *A61B 5/1455* | (2006.01) | |
| *A61B 5/1459* | (2006.01) | |

(52) U.S. Cl.
CPC ............ *A61B 1/0125* (2013.01); *A61B 1/018* (2013.01); *A61B 1/043* (2013.01); *A61B 1/0676* (2013.01); *A61B 5/0035* (2013.01); *A61B 5/0071* (2013.01); *A61B 5/0084* (2013.01); *A61B 5/015* (2013.01); *A61B 1/000094* (2022.02); *A61B 5/1459* (2013.01); *A61B 2560/0247* (2013.01)

(58) Field of Classification Search
CPC ..... A61B 5/1459; A61B 1/0005; A61B 1/005; A61B 1/0125; A61B 1/018; A61B 1/043; A61B 1/0676; A61B 1/000094; A61B 2561/0247; A61B 382/128
See application file for complete search history.

(56) References Cited

U.S. PATENT DOCUMENTS

| | | | |
|---|---|---|---|
| 4,597,392 A | | 7/1986 | Opitz et al. |
| 4,895,156 A | | 1/1990 | Schulze |
| 4,900,422 A | * | 2/1990 | Bryan ................. G01N 27/404 |
| | | | 204/415 |
| 4,947,850 A | | 8/1990 | Vanderkooi et al. |
| 5,071,417 A | | 12/1991 | Sinofsky |
| 5,178,141 A | | 1/1993 | Kanda |
| 5,318,023 A | | 6/1994 | Vari et al. |
| 5,495,850 A | | 3/1996 | Zuckerman |
| 5,515,864 A | | 5/1996 | Zuckerman |
| 5,593,899 A | | 1/1997 | Wilson et al. |
| 5,769,791 A | | 6/1998 | Benaron et al. |
| 5,785,658 A | | 7/1998 | Benaron et al. |
| 5,833,603 A | | 11/1998 | Kovacs et al. |
| 5,837,865 A | | 11/1998 | Vinogradov et al. |
| 5,860,917 A | | 1/1999 | Comanor et al. |
| 5,978,346 A | | 11/1999 | Mizuno et al. |
| 5,987,346 A | | 11/1999 | Benaron et al. |
| 6,099,466 A | | 8/2000 | Sano et al. |
| 6,163,714 A | | 12/2000 | Stanley et al. |
| 6,165,741 A | | 12/2000 | Wilson et al. |
| 6,173,197 B1 | | 1/2001 | Boggett |
| 6,174,291 B1 | | 1/2001 | McMahon et al. |
| 6,248,117 B1 | | 6/2001 | Blatter |
| 6,272,363 B1 | | 8/2001 | Casciani et al. |
| 6,274,086 B1 | | 8/2001 | Wilson et al. |
| 6,317,624 B1 | | 11/2001 | Kollias et al. |
| 6,362,175 B1 | | 3/2002 | Vinogradov et al. |
| 6,391,023 B1 | | 5/2002 | Weber et al. |
| 6,402,689 B1 | | 6/2002 | Scarantino et al. |
| 6,422,994 B1 | | 7/2002 | Kaneko et al. |
| 6,498,944 B1 | | 12/2002 | Ben-Haim et al. |
| 6,519,485 B2 | | 2/2003 | Wiesmann et al. |
| 6,631,286 B2 | | 10/2003 | Pfeiffer et al. |
| 6,652,452 B1 | | 11/2003 | Seifert et al. |
| 6,664,111 B2 | | 12/2003 | Bentsen et al. |
| 6,701,168 B1 | | 3/2004 | Wilson et al. |
| 6,975,898 B2 | * | 12/2005 | Seibel ................. A61B 1/07 |
| | | | 600/478 |
| 7,072,700 B2 | | 7/2006 | Yamamoto et al. |
| 7,139,600 B2 | | 11/2006 | Maki et al. |
| 7,311,661 B2 | | 12/2007 | Heinrich |
| 7,322,971 B2 | | 1/2008 | Shehada |
| 7,341,557 B2 | | 3/2008 | Cline et al. |
| 7,364,574 B2 | | 4/2008 | Flower |
| 7,420,151 B2 | | 9/2008 | Fengler et al. |
| 7,532,325 B2 | | 5/2009 | Ahmed et al. |
| 7,575,890 B2 | | 8/2009 | Wilson |
| 7,640,046 B2 | | 12/2009 | Pastore et al. |
| 7,720,521 B2 | | 5/2010 | Chang et al. |
| 7,720,532 B2 | | 5/2010 | Hashimshony et al. |
| 7,722,534 B2 | | 5/2010 | Cline et al. |
| 7,769,432 B2 | | 8/2010 | Klimberg et al. |
| 7,918,559 B2 | | 4/2011 | Tesar |
| 7,979,107 B2 | | 7/2011 | Lin et al. |
| 8,082,015 B2 | | 12/2011 | Yodh et al. |
| 8,118,206 B2 | | 2/2012 | Zand et al. |
| 8,185,176 B2 | | 5/2012 | Mangat et al. |
| 8,630,698 B2 | | 1/2014 | Fengler et al. |
| 8,647,605 B2 | | 2/2014 | Mangat et al. |
| 8,694,069 B1 | | 4/2014 | Kosa et al. |
| 8,961,403 B2 | | 2/2015 | Cline et al. |
| 9,044,179 B2 | | 6/2015 | Wilson et al. |
| 9,204,830 B2 | | 12/2015 | Zand et al. |
| 9,420,967 B2 | | 8/2016 | Zand et al. |
| 10,231,634 B2 | | 3/2019 | Zand et al. |
| 11,324,412 B2 | | 5/2022 | Zand et al. |
| 11,517,213 B2 | | 12/2022 | Zand et al. |
| 2002/0062061 A1 | | 5/2002 | Kaneko et al. |
| 2002/0137996 A1 | | 9/2002 | Chung et al. |
| 2002/0143294 A1 | | 10/2002 | Duchon et al. |
| 2002/0169394 A1 | | 11/2002 | Eppstein et al. |
| 2002/0173723 A1 | | 11/2002 | Lewis et al. |
| 2003/0014064 A1 | | 1/2003 | Blatter |
| 2003/0053697 A1 | | 3/2003 | Aylward et al. |
| 2003/0088162 A1 | | 5/2003 | Yamamoto et al. |
| 2003/0105300 A1 | | 6/2003 | Achilefu et al. |
| 2003/0163029 A1 | | 8/2003 | Sonnenschein et al. |
| 2003/0187319 A1 | | 10/2003 | Kaneko et al. |
| 2005/0131390 A1 | | 6/2005 | Heinrich et al. |
| 2005/0148832 A1 | | 7/2005 | Reghabi et al. |
| 2005/0152617 A1 | * | 7/2005 | Roche ................. G06T 7/30 |
| | | | 382/294 |
| 2005/0177035 A1 | | 8/2005 | Botvinick et al. |
| 2005/0240093 A1 | | 10/2005 | DeArmond |
| 2006/0195014 A1 | * | 8/2006 | Seibel ................. A61B 1/0008 |
| | | | 600/102 |
| 2006/0239921 A1 | | 10/2006 | Mangat et al. |
| 2007/0208252 A1 | | 9/2007 | Makower |
| 2007/0299309 A1 | | 12/2007 | Seibel et al. |
| 2008/0004531 A1 | | 1/2008 | Carp |
| 2008/0051646 A1 | | 2/2008 | Papkovsky et al. |
| 2008/0221648 A1 | | 9/2008 | Flower |
| 2008/0228037 A1 | | 9/2008 | Cline et al. |
| 2008/0285823 A1 | | 11/2008 | Bakker et al. |
| 2008/0287736 A1 | * | 11/2008 | Yamazaki ............ A61B 1/0057 |
| | | | 600/118 |
| 2008/0291397 A1 | | 11/2008 | Tesar |
| 2008/0310583 A1 | * | 12/2008 | Truyen ................. A61B 6/481 |
| | | | 378/19 |
| 2009/0054908 A1 | | 2/2009 | Zand et al. |
| 2009/0057543 A1 | * | 3/2009 | Ogikubo ............ A61B 5/0062 |
| | | | 250/234 |
| 2009/0130700 A1 | | 5/2009 | Ince et al. |
| 2009/0203994 A1 | | 8/2009 | Mangat et al. |
| 2009/0216097 A1 | | 8/2009 | Wilson et al. |
| 2009/0234248 A1 | | 9/2009 | Zand et al. |

(56) References Cited

U.S. PATENT DOCUMENTS

| | | |
|---|---|---|
| 2009/0259107 A1 | 10/2009 | Crenshaw et al. |
| 2009/0275818 A1 | 11/2009 | Rau et al. |
| 2009/0303317 A1 | 12/2009 | Tesar |
| 2010/0081895 A1 | 4/2010 | Zand |
| 2010/0158330 A1* | 6/2010 | Guissin .................. G06T 7/90 |
| | | 382/128 |
| 2010/0191081 A1 | 7/2010 | Shahidi |
| 2010/0198010 A1 | 8/2010 | Cline et al. |
| 2010/0202966 A1 | 8/2010 | Gross et al. |
| 2010/0210904 A1 | 8/2010 | Cline et al. |
| 2010/0222673 A1 | 9/2010 | Mangat et al. |
| 2010/0262017 A1 | 10/2010 | Frangioni |
| 2011/0021889 A1 | 1/2011 | Hoss et al. |
| 2011/0046480 A1 | 2/2011 | Yonezawa |
| 2011/0104071 A1 | 5/2011 | Lee et al. |
| 2011/0105869 A1 | 5/2011 | Wilson et al. |
| 2011/0178412 A1 | 7/2011 | Orlewski |
| 2011/0224519 A1 | 9/2011 | Adachi et al. |
| 2011/0230715 A1 | 9/2011 | Saito |
| 2011/0301443 A1 | 12/2011 | Yamaguchi et al. |
| 2012/0053433 A1 | 3/2012 | Chamoun et al. |
| 2012/0053434 A1 | 3/2012 | Saito |
| 2012/0116185 A1 | 5/2012 | Zand et al. |
| 2012/0116192 A1 | 5/2012 | Saito |
| 2012/0153188 A1 | 6/2012 | Barrett |
| 2012/0154566 A1 | 6/2012 | Kaku |
| 2012/0330351 A1 | 12/2012 | Friedman et al. |
| 2013/0054264 A1 | 2/2013 | Baronov et al. |
| 2013/0079607 A1 | 3/2013 | Gareau et al. |
| 2013/0102865 A1* | 4/2013 | Mandelis ........... G01N 21/1702 |
| | | 600/328 |
| 2013/0203865 A1 | 8/2013 | Wong et al. |
| 2013/0224874 A1 | 8/2013 | Vinogradov et al. |
| 2014/0194687 A1 | 7/2014 | Fengler et al. |
| 2014/0276008 A1 | 9/2014 | Steinbach et al. |
| 2014/0308210 A1 | 10/2014 | Mangat et al. |
| 2014/0342390 A1 | 11/2014 | Tsuji et al. |
| 2015/0282749 A1 | 10/2015 | Zand et al. |
| 2016/0045114 A1 | 2/2016 | Dacosta et al. |
| 2016/0073909 A1 | 3/2016 | Zand et al. |
| 2016/0310055 A1 | 10/2016 | Zand et al. |
| 2019/0209024 A1 | 7/2019 | Zand et al. |
| 2022/0257125 A1 | 8/2022 | Zand et al. |
| 2023/0363658 A1 | 11/2023 | Zand et al. |

FOREIGN PATENT DOCUMENTS

| | | |
|---|---|---|
| EP | 1868485 A4 | 10/2010 |
| EP | 1868485 B1 | 8/2016 |
| JP | S59500896 A | 5/1984 |
| JP | S63011135 A | 1/1988 |
| JP | 6-503487 A | 4/1994 |
| JP | 9-512446 A | 12/1997 |
| JP | 2022-529696 A | 9/2002 |
| JP | 2007503851 A | 3/2007 |
| JP | 2007097649 A | 4/2007 |
| JP | 2009538419 A | 11/2009 |
| JP | 2010-081898 A | 4/2010 |
| JP | 2010246779 A | 11/2010 |
| JP | 2010538785 A | 12/2010 |
| JP | 2011005002 A | 1/2011 |
| JP | 2011107129 A | 6/2011 |
| JP | 2011169688 A | 9/2011 |
| JP | 2011185842 A | 9/2011 |
| JP | 2014057898 A | 4/2014 |
| WO | 9203086 A1 | 3/1992 |
| WO | 95/28875 A1 | 11/1995 |
| WO | 1998/032088 A1 | 7/1998 |
| WO | 2000/018294 A1 | 4/2000 |
| WO | 200018294 A1 | 4/2000 |
| WO | 2002/007617 A2 | 1/2002 |
| WO | 2003/090630 A2 | 11/2003 |
| WO | 2006026396 A2 | 3/2006 |
| WO | 2006/113394 A2 | 10/2006 |
| WO | 2007050269 A2 | 5/2007 |
| WO | 2014153428 A1 | 9/2014 |
| WO | 2013094748 A1 | 4/2015 |

OTHER PUBLICATIONS

Okabe et al. "Intracellular temperature mapping with a fluorescent polymeric thermometer and fluorescence lifetime imaging microscopy," Nature Communications, 2012.

Non-Final Rejection dated Jan. 14, 2021, directed to U.S. Appl. No. 16/159,385; 7 pages.

Non-Final Rejection dated Aug. 31, 2020, directed to U.S. Appl. No. 16/165,222; 7 pages.

Final Rejection dated Apr. 21, 2021, directed to U.S. Appl. No. 16/165,222; 11 pages.

Non-Final Rejection dated Dec. 12, 2023, directed to U.S. Appl. No. 17/375,735; 12 pages.

Final Rejection dated Jul. 19, 2024, directed to U.S. Appl. No. 17/375,735; 13 pages.

Kinugasa, S. et al. "Development of a Fluorescent Temperature Sensor", Azbil Technical Review, Jan. 2012, p. 62-67 (8 pages) with English translation of Abstract.

Levedev et al., "Dendritic Phosphorescent Probes for Oxygen Imaging in Biological Systems," ACS Applied Materials and Interfaces, vol. 1, No. 6, Jun. 24, 2009, pp. 1292-1304.

Dunphy et al. "Oxyphor R2 and G2: phosphors for measuring oxygen by oxygen-dependent quenching of phosphorescense," Science Direct, Analytical Biochemistry 310, 2002, pp. 191-198.

Ronald Xu, et al. "Dual-mode Imaging of Cutaneous Tissue Oxygenation and Vascular Function", Journal of Visualized Experiments, Dec. 8, 2010 (8 pages).

Japanese Office Action in related Japanese Application No. 2017-503804 dated Jan. 17, 2019.

Japanese Office Action in related Japanese Application No. 2017-503804 dated Dec. 10, 2019.

Japanese Office Action in related Japanese Application No. 2017-503804 dated Nov. 4, 2020.

U.S. Non-Final Office Action in related U.S. Appl. No. 14/220,034 mailed Jun. 16, 2015.

U.S. Final Office Action in related U.S. Appl. No. 14/220,034 mailed Oct. 2, 2015.

U.S. Notice of Allowance in related U.S. Appl. No. 14/220,034 mailed Apr. 7, 2016.

Japanese Office Action in related Japanese Application No. 2016-505500 dated Feb. 26, 2018.

Japanese Office Action in related Japanese Application No. 2016-505500 dated Oct. 5, 2018.

Japanese Notice of Allowance in related Japanese Application No. 2016-505500 dated Apr. 24, 2019.

Japanese Office Action in related Japanese Application No. 2019-125937 dated Apr. 6, 2020.

Japanese Notice of Allowance in related Japanese Application No. 2019-125937 dated Aug. 11, 2020.

Japanese Office Action in related Japanese Application No. 2019-135416 dated Jun. 12, 2020.

Extended European Search Report in related European Application No. 14767896.5 dated Nov. 10, 2016.

European Office Action in related European Application No. 14767896.5 dated Dec. 19, 2019.

U.S. Non-Final Office Action in related U.S. Appl. No. 16/159,385 mailed Jan. 14, 2021.

Extended European Search Report in related European Application No. 15773739.6 dated Apr. 11, 2018.

European Office Action in related European Application No. 15773739.6 dated Oct. 27, 2020.

International Search Report in related International Application No. PCT/US2014/031267 dated Aug. 18, 2014.

International Preliminary Report on Patentability with Written Opinion in related International Application No. PCT/US2014/031267 dated Sep. 22, 2015.

International Search Report in related International Application No. PCT/US2015/024586 dated Jul. 13, 2015.

(56) References Cited

OTHER PUBLICATIONS

International Preliminary Report on Patentability with Written Opinion in related International Application No. PCT/US2015/024586 dated Oct. 12, 2016.
Chinese Office Action in related Chinese Application No. 201580029932.1 dated May 3, 2018.
Chinese Office Action in related Chinese Application No. 201580029932.1 dated Mar. 22, 2019.
Chinese Office Action in related Chinese Application No. 201580029932.1 dated Jul. 31, 2020.
Chinese Notice of Allowance in related Chinese Application No. 201580029932.1 dated Jan. 13, 2021.
U.S. Non-Final Office Action in related U.S. Appl. No. 15/203,634 mailed Oct. 11, 2016.
U.S. Final Office Action in related U.S. Appl. No. 15/203,634 mailed Aug. 15, 2017.
U.S. Advisory Action in related U.S. Appl. No. 15/203,634 mailed Dec. 11, 2017.
U.S. Non-Final Office Action in related U.S. Appl. No. 15/203,634 mailed Apr. 12, 2018.
U.S. First Action Interview Pilot Program Pre-Interview Communication in U.S. Appl. No. 14/679,707 dated Mar. 9, 2016 (23 pages).
U.S. Final Office Action in related U.S. Appl. No. 14/679,707 mailed Jun. 30, 2016.
U.S. Advisory Action in related U.S. Appl. No. 14/679,707 mailed Dec. 23, 2016.
U.S. Non-Final Office Action in related U.S. Appl. No. 14/679,707 mailed Feb. 7, 2017.
U.S. Non-Final Office Action in related U.S. Appl. No. 14/679,707 mailed Jul. 21, 2017.
U.S. Final Office Action in related U.S. Appl. No. 14/679,707 mailed Apr. 19, 2018.
International Search Report in related International Application No. PCT/US2006/013985 dated Dec. 7, 2007.
International Preliminary Report on Patentability with Written Opinion in related International Application No. PCT/US2006/013985 dated Mar. 10, 2009.
Canadian Office Action and Examination Search Report issued in corresponding Canadian Patent Application No. 2,604,563, dated Oct. 24, 2014.
Communication pursuant to Article 94(3) EPC dated Oct. 31, 2023, directed to EP Patent Application No. 15773739.6; 5 pages.
Decision of Refusal mailed May 20, 2021, directed to Japanese Application No. 2017-503804; 6 pages.
Notification of the First Office Action mailed Aug. 5, 2023, directed to CN Patent Application No. 202011473160.X; 20 pages.
Communication pursuant to Article 94(3) EPC dated Jul. 7, 2022, directed to EP Patent Application No. 15773739.6; 5 pages.
Rejection Decision dated Apr. 3, 2024, directed to CN Patent Application No. 202011473160.X; 13 pages.
Communication pursuant to Article 94(3) EPC dated Aug. 16, 2024, directed to EP Patent Application No. 15 773 739.6; 5 pages.
Notice of Reasons for Refusal dated Jun. 16, 2023, directed to JP Patent Application No. 2022-092169; 4 pages.
Notice of Reasons for Rejection dated Jul. 6, 2022, directed to JP Patent Application No. 2017-503804; 18 pages.
Fischer, G. et al. (May 2005) "Intra-operative Ischemia Sensing Surgical Instruments," Complex Medical Engineering; 6 pages.
European Communication Pursuant to Article 94(3) EPC, issued in European Patent Application No. 06758332.8-2319, mailed on Feb. 5, 2014; 3 pages.
European Communication Pursuant to Article 94(3) EPC, issued in European Patent Application No. 06758332.8-2319, mailed on Dec. 5, 2012; 5 pages.
Canadian Office Action and Examination Search Report issued in corresponding Canadian Patent Application No. 2,604,563, mailed on Oct. 24, 2014; 5 pages.

Chinese Notification of First Office Action issued in corresponding Chinese Patent Application No. 200680021505.X, mailed on Sep. 14, 2010; 16 pages.
Chinese Notification of Third Office Action issued in corresponding Chinese U.S. Appl. No. 11/918,456.X, mailed on Sep. 7, 2012; 6 pages.
Chinese Notification of Fourth Office Action issued in corresponding Chinese Patent Application No. 200680021505.X, mailed on Feb. 8, 2013; 24 pages.
Chinese Notice of Allowance issued in corresponding Chinese U.S. Appl. No. 11/918,456.X, mailed on May 16, 2013, 4 pages.
Chinese Notification of First Office Action issued in corresponding Chinese U.S. Appl. No. 11/918,456.7, mailed on Mar. 27, 2015; 11 pages.
Product Description: SPY Elite: SPY Imaging for Open Surgery, available in NOVADAQ.com, retrieved on Apr. 24, 2015 at http://novadaq.com/products/spy-elite; 1 page.
Product Description: PINPOINT Endoscopic Fluorescence Imaging: PINPOINT Imaging for Minimally Invasive Surgery, available in NOVADAQ.com, retrieved on Apr. 24, 2015 at http://novadaq.com/products/pinpoint-endoscopic-fluorescence-imaging; 2 pages.
Company Description: Technologies and Intellectual Property: SPY Imaging Technology, available in NOVADAQ.com, retrieved on Apr. 24, 2015, at http://novadaq.com/company/technologies/ip.
European Search Report issued in European Patent Application No. 06758332.8-2319, mailed Sep. 21, 2010.
Chinese Office Action issued in Chinese Patent Application No. 200680021505.X, dated Dec. 19, 2011.
International Preliminary Report on Patentability issued in corresponding International Patent Application No. PCT/US2006/013985, dated Dec. 7, 2007.
Non-Final Rejection dated Mar. 6, 2012, directed to U.S. Appl. No. 11/918,456; 7 pages.
Final Rejection dated Dec. 12, 2012, directed to U.S. Appl. No. 11/918,456; 11 pages.
Non-Final Rejection dated May 9, 2014, directed to U.S. Appl. No. 11/918,456; 7 pages.
Non-Final Rejection dated Dec. 2, 2014, directed to U.S. Appl. No. 11/918,456; 7 pages.
Notice of Allowance dated Jul. 31, 2025, directed to U.S. Appl. No. 11/918,456; 8 pages.
Notification of Second Chinese Office Action dated Jan. 6, 2016, issued in corresponding Chinese Application No. 20130328575.7.
Office Action issued in Canadian Patent Application No. 2,604,563, dated Feb. 23, 2018.
Supplementary European Search Report for European Patent Application No. 06758332.8-2319, dated Sep. 13, 2010.
Canadian Office Action dated Feb. 22, 2017 issued in Canadian Patent Application No. 2,604,563.
Chinese Office Action dated May 2, 2017, issued in Chinese Application No. 201310328574.7.
Chinese Office Action dated Sep. 28, 2016 issued in Chinese Patent Application No. 201310328574.7.
Extended European Search Report dated Sep. 5, 2016 issued in European Patent Application No. 16001279.5.
Non-Final Rejection dated Apr. 19, 2016, directed to U.S. Appl. No. 14/949,846; 11 pages.
Final Rejection dated Aug. 23, 2016, directed to U.S. Appl. No. 14/949,846; 6 pages.
Non-Final Rejection dated May 19, 2017, directed to U.S. Appl. No. 14/949,846; 7 pages.
Final Rejection dated Mar. 13, 2018, directed to U.S. Appl. No. 14/949,846; 9 pages.
Notice of Allowance dated Oct. 19, 2018, directed to U.S. Appl. No. 14/949,846; 6 pages.
Non-Final Rejection dated Sep. 16, 2020, directed to U.S. Appl. No. 16/299,808; 6 pages.
Notice of Allowance dated Jan. 11, 2012, directed to U.S. Appl. No. 16/299,808; 9 pages.
Notice of Allowance dated Aug. 4, 2022, directed to U.S. Appl. No. 17/739,982; 13 pages.

(56) References Cited

OTHER PUBLICATIONS

Non-Final Rejection dated Feb. 29, 2024, directed to U.S. Appl. No. 18/076,131; 8 pages.

* cited by examiner

APPARATUS, SYSTEMS, AND METHODS FOR MAPPING OF TISSUE OXYGENATION

CROSS REFERENCE TO RELATED APPLICATIONS

This application is a continuation of U.S. application Ser. No. 16/165,222, filed Oct. 19, 2018, which is a continuation of U.S. application Ser. No. 14/679,707, filed Apr. 6, 2015, and claims the benefit of the filing date of U.S. Provisional Application Nos. 62/061,079, filed Oct. 7, 2014, and 61/975,742, filed Apr. 5, 2014, the contents of which are hereby incorporated by reference in their entireties.

GOVERNMENT INTEREST

This invention was made, in whole or in part, with Government Support under National Institutes of Health grant CA153571. The Government has certain rights in the invention.

TECHNICAL FIELD

The present invention relates to surgical instruments and medical imaging systems, and the molecular agents used by the instruments and systems; specifically to surgical instruments and imaging systems with sensors used to detect properties of biological tissue, and a system for exploiting the information gathered by the sensors. A sensing system can be configured to obtain a mapping of physiologic properties of tissue at multiple locations. Further, information from multiple sensing modalities can be used together to enable improved measurement accuracy.

BACKGROUND

A living organism is made up of cells. Cells are the smallest structures capable of maintaining life and reproducing. Cells have differing structures to perform different tasks. A tissue is an organization of a great many similar cells with varying amounts and kinds of nonliving, intercellular substances between them. An organ is an organization of several different kinds of tissues so arranged that together they can perform a special function.

Surgery is defined as a branch of medicine concerned with diseases requiring operative procedures.

Ninety five percent of the time colorectal cancer develops by a well understood series of genetic mutations over a 10-15 year time frame beginning as a growth, or polyp. Over their lifetime, approximately one third to one half of adults will develop one or more polyps, approximately ten percent of which will continue to become cancer. Therefore the overwhelming majority of colorectal cancers can be avoided by identification and removal of polyps at an early stage before malignant conversion. Endoscopy is the predominant means by which the US population is screened for benign and malignant polyps. While colonoscopy can detect up to 95% of cancerous lesions, polyps are missed approximately 25% of the time, even utilizing current "enhanced endoscopy" technology.

BRIEF SUMMARY OF THE INVENTION

The present invention relates to medical devices and systems capable of measuring physiologic properties of tissue. In one embodiment of the system, tissue oxygenation is assessed utilizing the technique of oxygen dependent quenching of phosphorescence. Whereby phosphorescence is produced from native biologic tissue, or via an injected phosphorescent oxygen sensing molecular probe. In alternative embodiments, other phosphors or molecular markers may be used to localize specific targets or assess other physiologic parameters. Techniques and instrument configurations for assessing oxygenation are disclosed in PCT Patent Application No. PCT/US14/31267 titled Apparatus, Systems and Methods for Determining Tissue Oxygenation, the disclosure of which is incorporated herein by reference in its entirety.

The present invention includes an imaging system that resolves and maps a physiologic condition, or proxy thereof. The imaging system utilizing information obtained from two or more sensing modalities to resolve the physiologic condition. The additional modalities used in conjunction provide improved accuracy of absolute measurements in the physiologic condition or measurement. One embodiment of the invention takes the form of a multi-modality imaging system, wherein one modality assesses the phosphorescent and/or fluorescent lifetime decay of a medium and another modality assesses temperature at or near the medium. In one configuration, the medium is an injectable probe with a phosphorescent lifetime that relates to nearby/resident/proximate/field oxygen concentration/tension of the subject biologic tissue; the temperature measurement allows for selection of a precise temperature-dependent calibration coefficient of the probe's lifetime used to more accurately resolve oxygenation.

An embodiment of the imaging system comprises an optical sensor configured for detection and measurement of the lifetime of the decay of light emitted by a phosphorescent and/or fluorescent medium resulting from illumination of the medium at one or more excitation wavelengths, and further comprising a temperature sensor for detecting the temperature at one or more points in the field of view of the optical sensor. The system further comprising a processor configured to use temperature measurement to compensate for temperature-dependent lifetime variation of the phosphorescent and/or fluorescent response. An embodiment of the invention includes a phosphorescent lifetime imaging (PLI) system, wherein the system comprises both an optical detector for mapping phosphorescent lifetime and an optical detector for detecting temperature. The system additionally capable of registering the temperature and lifetime images, and utilizing both phosphorescent lifetime and temperature at each mapped point to determine the corresponding oxygenation concentration(s) in the subject tissue.

An embodiment of the present invention includes an imaging system configured for generating a map of biologic tissue oxygenation based on phosphorescent lifetime of an injectable probe in a region. The system comprising an optical sensor such as a camera-based device configured for detecting the lifetime of the phosphorescent decay of the phosphorescent probe in the region, and further comprising a temperature sensor configured to map the temperature of the region. In one configuration, the temperature sensor is a thermal imaging camera. The correspondence between measurement locations by both sensors in the region are identified so as to compensate for temperature-dependent calibration from lifetime to oxygenation.

An embodiment of the present invention is an endoscopic system (such as, but not limited to, a colonoscopic system) configured for measuring tissue oxygenation based on quenching of the phosphorescent/fluorescent lifetime of an injectable phosphorescent/fluorescent probe by surrounding oxygen, and generating a map of the oxygenation. The endoscopy system further comprises a means of detecting temperature in the region corresponding to the map of oxygenation, wherein the oxygen-sensing endoscopic system is configured to compensate for temperature-dependent parameters of the oxygenation measurements based on thermal measurements of the temperature detectors. Another embodiment of the invention takes the form of a sensing system that operates independently from a scope such as an endoscope or colonoscope, and operates in conjunction with the scope. The system is configured to map both phosphorescent lifetime and temperature at the tip of the scope and use the temperature maps in conjunction with the phosphorescent lifetime maps to generate temperature-compensated absolute tissue oxygenation maps. One configuration of the independently operating sensing system takes the form of an oxygen sensing system that incorporates a micro camera-based thermal imaging cameras. An alternate configuration of the independently operating sensing system takes the form of an oxygen sensing system comprising a thermal camera coupled to a coherent fiber optic imaging bundle with transmission in the infrared range that enables remote sensing of temperature.

An embodiment of the present invention includes an imaging system based on a probe using phosphorescence and/or fluorescence. The probe may be a nanosensor molecule, quantum dots, or other molecular tag or marker. The probe may be injectable systemically or locally, or otherwise introduced into the body. An alternate embodiment of the imaging system is configured to image natural, or autofluorescence of tissue. The imaging system further comprising a means for measuring at least one or more physiologic or environmental parameters and using the measurement to adjust the calibration of the final measurement image to compensate for the environmental or physiologic parameters. The environmental and physiologic parameters may include at least one of: temperature, pH, concentration of other compounds of absorbers present, measurements of additional probes, and measurement of a reference probe or probe with a secondary reference emission. An embodiment of the imaging system is configured to generate an image representing a physiologic parameter based on a phosphorescence and/or fluorescence response from an introduced probe or from naturally occurring interactions. The system is capable of utilizing temperature or other environmental or physiologic parameter to compensate for the measurement represented in the image.

An embodiment of the present invention describes a system and method for generating and combining images in an image overlay or other augmented reality view. The present invention includes an approach for overlay of physiologic parameters on endoscopic video images. It further comprises a method for registering oxygenation maps (or maps of other physiologic properties) with visible light or other video images. An embodiment of the present invention incorporates a method for registering oxygenation maps or the corresponding precursor lifetime maps to thermal maps/images, and utilizing the registered temperature information to compensate for temperature-dependent variation in oxygenation measurements. One method for the registration includes acquiring images from multiple cameras using wavelengths of light, such as those in the near infrared (NIR) band, that are detected by each camera (such as a visible light endoscopy camera and physiologic parameter sensing cameras), and using the mutual information and/or other features between the images for registration. Included in this invention is an embodiment of the invention where at least two of the following are registered using the approach: thermal image, visible light image, and phosphorescent lifetime image. In one configuration of the present invention, an endoscopic imaging instrument is configured to map tissue oxygenation of the gastrointestinal tract.

The system is further configured to identify suspect lesions, such as pre-cancerous polyps or lesions. Incorporated is a method for distinguishing lesions such as polyps from healthy intestinal wall tissue utilizing pattern matching of static images of phosphorescent lifetime or oxygenation. Static images refer to individually captured images, as opposed to a time series of images; static images may be continuously updated. An alternate method for distinguishing lesions from healthy tissue utilizes dynamic changes in lifetime of a time series of images. Included in the present invention is an instrument configured to map tissue oxygenation and use the information to guide localization at least one of non-cancerous, pre-cancerous, or cancerous lesions. A further embodiment is an endoscopic imaging system configured to generate a map of tissue oxygenation wherein the oxygenation map guides localization of the lesions. The system incorporates a method for identifying potentially suspect lesions (such as polyps) through mapping of the tissue oxygenation, and optionally generating an alert. An endoscopic imaging instrument configured to map tissue oxygenation of the intestinal wall. The system further configured to identify suspect lesions, such as pre-cancerous polyps. One configuration of the system incorporates a method for distinguishing polyp from healthy intestinal wall tissue utilizing pattern matching of static images of phosphorescent lifetime or oxygenation. An alternate method for distinguishing polyp from healthy intestinal wall tissue utilizes dynamic changes in lifetime of a time series of images. A further configuration of the system also incorporates contouring, segmentation, and boundary detection. The detection may incorporate techniques such as active contour models, level set methods, edge detection, or others. An approach for using histograms of the oxygenation within the identified region to further identify or classify properties of the lesion is also included. In an alternate configuration, the system is configured for detecting anatomy utilizing phosphorescence lifetime imaging (or related approach), and may be further configured to determine the location of and/or highlight vasculature.

An embodiment of the invention includes a sensing scope that is integrated into or an accessory to a standard endoscopic system. The scope may couple with or be introduced through a working channel or instrument port on a traditional endoscope. Further, the sensing scope being capable of providing multi-modality imaging, including but not limited to, phosphorescent and/or fluorescent lifetime, visible light images, and temperature measurements. The invention further includes a method for tracking features and maintaining alignment of an acquired oxygen map (or other property) after removal of, or disabling of, a sensing instrument or scope. The method maintains the location identified on a visible light image such that the image may be used to guide an intervention, such as biopsy or removal of a lesion. The method further maintains location data of the lesion using registration techniques to allow for movement of the visible light scope during the intervention.

One embodiment incorporates an adapter or coupler for interfacing with a preexisting or standard endoscopy system, wherein the coupler introduces modulated light for the sensing system through the existing light channels. Further, an adapter enables thermal imaging through introduced or preexisting imaging channels, wherein the channels may be rigid light guides or flexible fiber optic bundles. One embodiment incorporates a flexible endoscopy device wherein a flexible coherent fiberoptic bundle that may be utilized for both infrared thermal imaging and illumination. An alternate embodiment is contemplated wherein a flexible coherent fiberoptic bundle may be utilized for both PLI and thermal imaging. The fiber bundles may be configured to have sufficiently high transmission of infrared radiation corresponding to the sensitive wavelengths of thermal imagers (i.e., up to approximately 15 um). An embodiment comprises a flexible endoscopy system where an illumination fiber bundle is multiplexed to enable its use in both illumination and sensing. The fiber may be used for white light illumination or photo-excitation of a light emitting probe. The fiber may be used for receiving a white light image, phosphorescent emission image, or infrared thermal image.

An embodiment of the present invention teaches a camera-based phosphorescent lifetime imaging system, wherein the light source for exciting the phosphorescent probe also comprises such as broadband white light emitters. The system capable of both providing visible light images and PLI measurements, wherein output from the light sources may be modulated as required. Further contemplated is a camera-based phosphorescent lifetime imaging system, wherein a light source for exciting the phosphorescent probe comprises emitters circumferentially located around the camera lens. The circumferentially located emitters, referred to as the ring light, enable directed light to the region of interest in the camera's field of view. The ring light may incorporate one or more lenses. The ring light may incorporate both light sources for exciting the phosphorescent response and for providing visible light. An alternate embodiment is contemplated where the combined light source is externally located and directed at the region of interest, and in one further embodiment the light source is mounted alongside or incorporated into procedure/operating room (OR) lights.

The present invention teaches the use of at least two unique probe types together in a medium, wherein one serves as a reference to compensate the readings of the other for improved accuracy. In one embodiment of the approach a temperature-dependent probe, not affected significantly by other factors, is introduced alongside an oxygen-sensitive probe and the response of the temperature-dependent, substantially oxygen insensitive probe is used to compensate for measurements of the oxygen-sensitive probe. In one configuration, a fluorescent or phosphorescent probe that has a temperature dependent decay lifetime that is introduced alongside an oxygen-sensitive probe, wherein the two probes have distinctly different excitation and/or emission wavelengths. In another embodiment, two oxygen-dependent probe types with different temperature dependence are introduced, and the lifetimes from the probes are used to accurately produce an oxygenation measurement that is robust to temperature variations, wherein the two probes have distinctly different excitation and/or emission wavelengths. A further embodiment wherein two probes are mixed and of a configuration that allows a substantially similar distribution in the tissue upon injection. The probes may be of the same structure with different core materials having different spectral and temporal response characteristics. The lifetime of the two probes may be read in an alternating pattern, or one may be read repeatedly for real-time sensing while the other read at a reduced rate for temperature compensation.

The present invention also can include a surgical stapler anvil with incorporated oxygen sensing capabilities based upon phosphorescent lifetime. A further embodiment wherein the anvil comprises a camera that is utilized in the sensing. One configuration of the surgical stapler anvil incorporates oxygen mapping capabilities at two or more points based upon phosphorescent lifetime. A further embodiment wherein the anvil incorporates temperature sensing, and the temperature map is used to compensate for the map of oxygen measurements. A sensing instrument with integrated needles for microinjection of a probe is taught in the present invention. One configuration further comprises an injector that couples with a surgical stapler anvil to inject a medium into tissue at or near the anvil's working surface (i.e., staple form surface); the medium containing one or more phosphorescent oxygen sensing probe variants. The invention also includes a standalone instrument with incorporated oxygen sensing capabilities based upon phosphorescent lifetime that couples to surgical stapler anvil to assess oxygenation of tissue at or near the anvil's working surface (i.e., staple form surface). The instrument containing one or more sensors configured to rotate or otherwise fully image the anastomosis. Also included is an interrogator wand with an integrated injector for delivering probe and/or sensing tissue oxygenation. The injector may enable injection internal to the tissue, such as inside a colonic wall, or external injection, such as externally through a colonic wall. The instruments further comprising a means for measuring temperature of tissue at the working surface. In a further embodiment of the invention, a camera-based phosphorescent lifetime imaging system comprises a means for attaching an anvil of a surgical stapler, wherein the attachment is through a quick-release type coupler to the anvil. The system is configured to generate an oxygenation map of the anastomosis during surgery. The system further comprising a thermal imaging camera imaging substantially the same region as the PLI system and using the measurements to enhance accuracy of oxygenation measurements.

One embodiment of the current invention is based upon a small secondary imaging system, such as a CMOS microcamera, which fits down the working channel of an existing colonoscope to generate an oxygen map of the colonic wall. The system displays the map and/or highlights suspicious lesions using graphic overlay on synchronously acquired traditional scope video images. If a suspicious lesion is identified the system will allow for exchange of the oxygen mapping camera for another instrument, while retaining/tracking the lesion highlighted on the video monitor. Oxygen mapping in one embodiment will be realized using phosphorescent lifetime imaging (PLI) of an oxygen-sensitive, systemically injected molecular probe. In one embodiment of the present invention, temperature sensing is coupled with PLI to generate a temperature-compensated map of oxygen concentration. The invention is not restricted to only coupling with a colonoscope to assess cancerous lesions in colonic wall tissue; the present invention includes all scope and camera types and configurations including flexible and rigid, monitoring or visualization of all internal and external tissues, and identification of any type of variation in the parameters of the tissue.

One representative application of the present invention is in the creation and monitoring of tissue flaps. Cancer of various types, i.e., breast, skin, etc., often cause removal of significant volumes of tissue during an attempt at curative resection. Traumatic injury may result in severed limbs or avulsed portions of tissue. The resulting tissue loss is often replaced by native tissue transposed from other parts of the patient's body. Free tissue flaps are flaps that are completely removed from their native position along with the supplying vascular pedicle. The free flap vasculature is then reconnected to vessels near the tissue void. The vascular anastomosis may fail due to leakage, stricture, or occlusion from inappropriate clot formation. The present invention enables resolution of flap oxygenation through a map of the tissue oxygenation, both for the intra-operative confirmation of tissue perfusion, and post-operative monitoring. Current technology is limited to qualitative measures of blood flow. The present invention presents real time quantitative assessment of tissue oxygenation. An embodiment of the invention couples a camera-based phosphorescent lifetime detector with a thermal imaging camera, wherein a registered temperature map is used to correct for the calibration coefficients used to convert phosphorescent lifetime to oxygen concentration. A similar configuration may be used for monitoring both internal and external tissue. Another example application is in diagnosing, assessing, or monitoring the treatment of peripheral vascular disease (PVD).

Other potential applications include but are not limited to the monitoring/recording of a transplanted organ or appendage, intra-cranial, intra-thecal, intra-ocular, intra-otic, intra-nasal, intra-sinusoidal, intra-pharyngeal, intra-laryngeal, intra-esophageal, intra-tracheal, intra-thoracic, intra-bronchial, intra-pericardial, intra-cardiac, intra-vascular, intra-abdominal, intra-gastric, intra-cholecystic, intra-enteric, intra-colonic, intra-rectal, intra-cystic, intra-ureteral, intra-uterine, intra-vaginal, intra-scrotal; intra-cerebral, intra-pulmonic, intra-hepatic, intra-pancreatic, intra-renal, intra-adrenal, intra-lienal, intra-ovarian, intra-testicular, intra-penal, intra-muscular, intra-osseous, and intra-dermal physiologic/biomechanical parameters.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

DETAILED DESCRIPTION OF THE INVENTION

Figure 1:
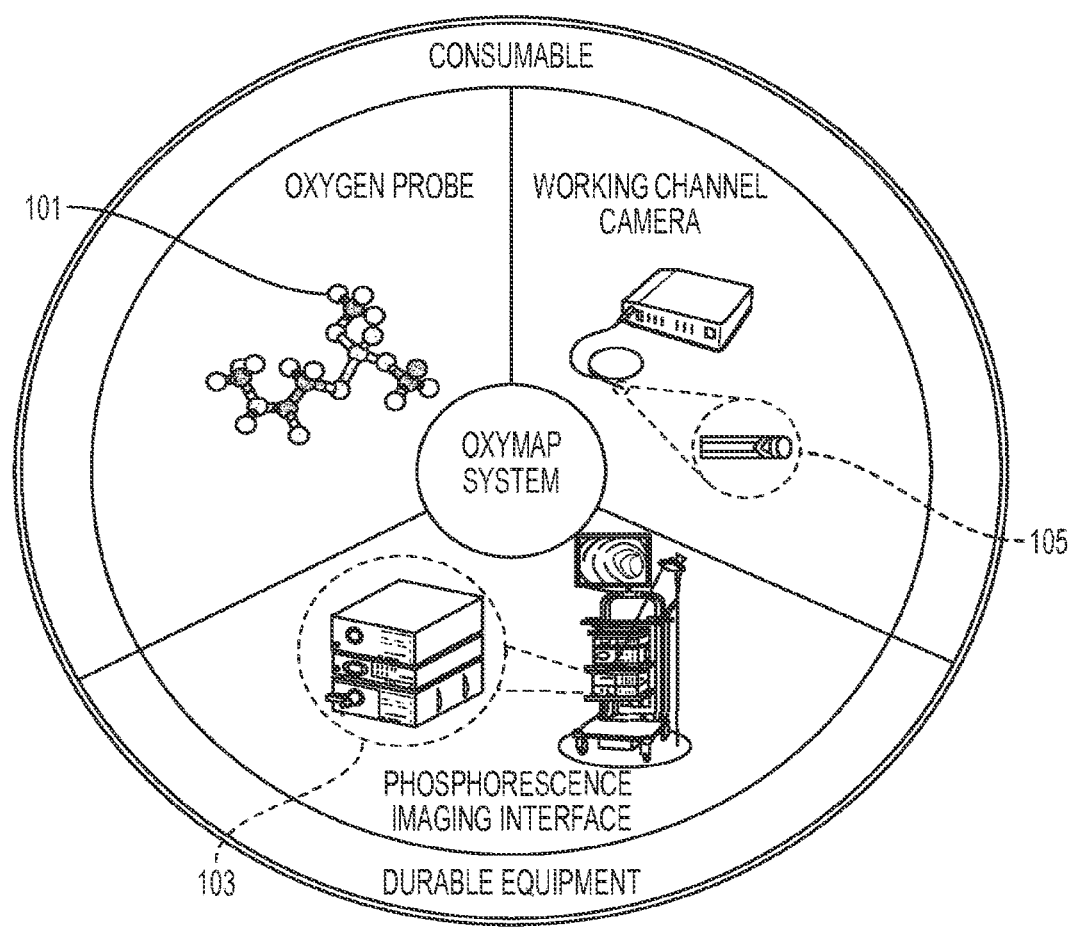
FIG. 1 shows a representation of the components of one embodiment of the present invention.

Tissue parameters can be measured by a variety of methods. One technique utilized by the present invention measures tissue oxygenation levels via utilizing oxygen dependent quenching of phosphorescence via a systemic or locally injected phosphorescent oxygen sensing molecular probe for oxygen measurements as disclosed in U.S. Pat. Nos. 4,947,850, 5,837,865, 6,362,175, 6,165,741, 6,274,086, 7,575,890 and US Patent Application Publication No. 2013/0224874, which disclose measurement methods, the disclosures of which are incorporated herein by reference in their entireties. The phosphorescent oxygen sensing probe comprises a phosphorescent metalloporphyrin core encapsulated inside hydrophobic dendrimers, which form a protecting shell that isolates the chromophore from direct contact with the environment, controls oxygen diffusion, and enables control over the probe's dynamic range and sensitivity. The metalloporphyrin core can be constructed with different elements. Palladium and platinum are two elements that can be utilized. An advantage of a platinum based core over a palladium based core is its quantum efficiency. The increase in the quantum efficiency of the phosphor allows for a significant increase of light output when compared to the Pd based molecule; more light returned per molecule allows for the use of fewer molecules to achieve the same signal returned to the device. Alternatively, injection of the same amount of molecule enables the use of less sensitive (less expensive) photo-detectors. Peripheral PEGylation of the dendritic branches ensures high aqueous solubility of the probe whilst preventing interactions with biological macromolecules. The overall size of the molecular probe affects the probe's ability to be cleared by the kidney. Faster clearance limits the agent's exposure to the patient. The size can be varied through the modification of the dendrimer length, number of dendrimers, and the size of PEGs/extent of PEGylation.

In one embodiment of the probe, the core, Pd-meso-tetra-(3,5-dicarboxyphenyl)tetrabenzoporphyrin (PdTBP), is encapsulated by eight generation 2 poly-arylglycine (AG2) dendrons; each of which are PEGylated with monomethoxy-polyethyleneglycol amine (PEG-NH2) groups (Av. MW 1,000 Da), having on average 21-22 monomeric —(CH2CH2O)— units. The molecular weight of the probe dendrimer was found to be in the range of −26,000-44,000 Da with a maximum of 35,354 Da as determined by MALDI mass spectroscopy. The phosphorescence quenching method relies on the ability of molecular oxygen (O2) to quench phosphorescence of excited triplet state molecules in the environment. In biological systems phosphorescence quenching by oxygen occurs in a diffusion controlled fashion and is highly specific to O2, since O2 is the only small-molecule dynamic quencher present in sufficiently high concentrations. The dependence of the phosphorescence lifetime (T) on the partial pressure of oxygen (pO2) through the range of biological concentrations is well described by the Stern-Volmer equation: $1/\tau = 1/\tau_0 + k_q \times pO_2$, where $\tau$ is the phosphorescence lifetime at a specified oxygen pressure pO2, $\tau_0$ is the phosphorescence lifetime in the absence of oxygen (pO2=0), and kq is the quenching constant. One molecular oxygen probe has a quenching constant, kq, of approximately 326 mmHg$^{-1}$ s$^{-1}$, and a $\tau_0$ of 210 µs over the range of physiologic pH, 6.2-7.8, and constant temperature of 36.5° C.

The calibration parameters of the probe, kq and T0, change linearly with respect to temperature. The quenching constant, kq, increases from 211 mm Hg$^{-1}$ s$^{-1}$ to 338 mmHg$^{-1}$ s$^{-1}$ with the rise of temperature from 22° C. to 38° C., which corresponds to the temperature coefficient of 7.8 mm Hg$^{-1}$ s$^{-1}$/° C. The absorption spectrum of the probe has maxima at approximately 448 nm and 637 nm with a phosphorescence emission maximum of 813 nm. Excitation at multiple wavelengths confers an application specific advantage of being able to interrogate and distinguish tissue properties at differing penetration depths or layers. A combination of multiple pO2 values in a field of view will manifest itself as a combination of lifetimes (a sum of exponential decays); multiple pO2 values and corresponding concentrations can be determined through means described herein.

Due to the dependence of measured phosphorescent lifetime on temperature, it is critical to assess the temperature at the measurement site and use that information to apply the appropriate relationship between phosphorescent lifetime and oxygen concentration. By measuring the temperature at a measurement point, the appropriate temperature-dependent quenching coefficient kq may be selected to allow improved accuracy of oxygen concentration measurement at that point. Although average temperature of a measurement region may be used to improve accuracy, further location-dependent compensation may be obtained through mapping the temperature at multiple points and relating the correspondence of those points to lifetime measurements when converting to oxygen concentration. Note that oxygen concentration and oxygenation may be used interchangeably in this disclosure and both relate to the amount of oxygen present in the tissue.

An embodiment of the invention is intended to detect a quantitative difference in interstitial tissue oxygenation of non-cancerous, pre-cancerous, and cancerous lesions when measured against the surrounding normal tissue. A specific embodiment further described aims to identify the lesions in the gastrointestinal tract. One application of the invention is directed toward enhancing the detection of pre-cancerous colonic polyps. Through the mapping of interstitial tissue oxygenation, during video colonoscopy, the invention aims to improve detection of pre-neoplastic, and neoplastic lesions during screening colonoscopy when compared to traditional white light and "enhanced" endoscopic techniques. Furthermore the invention aims to differentiate lesions of various malignant potential based on patterns of tissue oxygenation. Note for the purposes of this application, "white light" and "visible light" imaging may be used interchangeably. By simultaneously mapping the temperature in the same region of interest, we can improve sensing accuracy by using a temperature-dependent calibration of lifetime to tissue oxygenation. Note that for the purpose of this application, phosphorescent lifetime images/imaging (PLI) refer to the precursor used for calculating a physiologic parameter such as oxygenation and may be an actual calibrated lifetime such as measured in microseconds, or may be represented by related raw data including clock cycles, camera frames, phase delay, or other measurement parameters.

There is currently no clinically practical method of quantitatively assessing tissue oxygenation during colonoscopy or method of exploiting such information to improve polyp detection. The approaches may also be used for various other tissue imaging, including but not limited to, gastrointestinal imaging to guide surgical procedures such as a colonic or rectal anastomosis. The term imaging refers to taking measurements at multiple locations. This includes, but is not limited to, a 2D map such as a camera-based sensor or an array of discrete points such as multiple sensor elements on an instrument.

FIG. 1 shows a representation of the components of one embodiment of the present invention, an endoscopic system 100 comprising an oxygen sensing molecular probe 101, a phosphorescent lifetime imaging interface 103, and a secondary camera 105. The system aids in the detection of non-cancerous, pre-cancerous, and cancerous lesions through exploitation of oxygen differences that exist between healthy tissue and lesions. The system generates quantitative oxygen mappings of the gastrointestinal tract. An example of a lesion is a colonic polyp found in the colon. The oxygen-sensitive phosphorescent oxygen sensing probe 101 is a nanosensor that is injected systemically into the bloodstream or locally into the tissue interstitial space. The phosphorescent lifetime imaging interface 103 determines tissue oxygenation based on the optical response (related to oxygen-dependent quenching of phosphorescent lifetime) of the phosphorescent probe 101. Phosphorescent lifetimes are imaged by a secondary camera 105 which is passed through the working channel of a traditional scope, such as a colonoscope. In one embodiment, the secondary imaging system 105 is small micro-camera endoscope that is inserted into the proximal end of a working channel of a traditional colonoscope and passed to the distal end of the colonoscope. The camera may be integrated into a flexible cannula and may be a single use or limited lifetime device. In another embodiment, the secondary imaging system comprises a fiberoptic imaging bundle that is inserted into the proximal end of a working channel and passed distally. The proximal end of the imaging bundle is coupled to a camera. In another embodiment the proximal end of the imaging bundle is coupled to an image intensifier which is coupled to a camera. The camera itself may employ image intensifying optics. The light passing into or out of the imaging bundle may pass though optical filters. The system may further comprise a thermal imaging system capable of mapping the temperature in the region of oxygenation measurement. In one embodiment, infrared radiation is passed through a coherent fiberoptic bundle to a thermal imaging camera. The fiber optic bundle may be the same as that used in the secondary imaging system, a bundle also used for illumination, or an alternate bundle.

The present invention includes configurations of oxygen-dependent quenching molecular probes 101 that enables controlled dwell time in the body or a portion thereof. Controlled variation of the size and shape of the probe affect dwell time and clearance rates. In one embodiment, the probe is excreted from the body in under 24 hours. The molecular probe 101 may be integrated into or coupled with fully or partially bioabsorbable beads or other objects so as to maintain sufficient probe at a site for an extended period following injection. An alternate approach of maintaining the probes at a site or directing the probes towards a site includes coupling a molecular probe with a magnetic carrier for control of its position or to maintain sufficient probe at a site for an extended period. The present invention may also incorporate phosphors and other markers for various physiologic parameters other than oxygenation, such as glucose levels, pH, lactate, or disease markers. The measurement of multiple physiologic parameters can occur simultaneously.

Figure 2A:
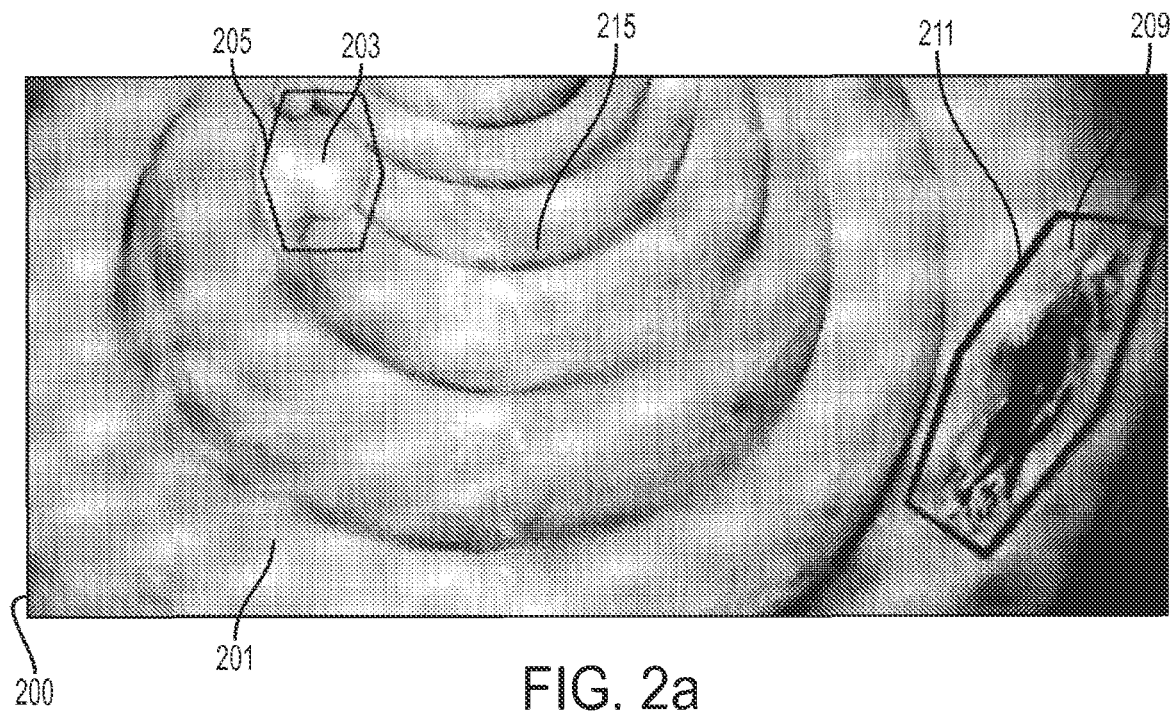
FIG. 2a shows an embodiment of the present invention wherein the system generates a graphic overlay to identify lesion location on synchronously acquired endoscopic video images.
Figure 2B:
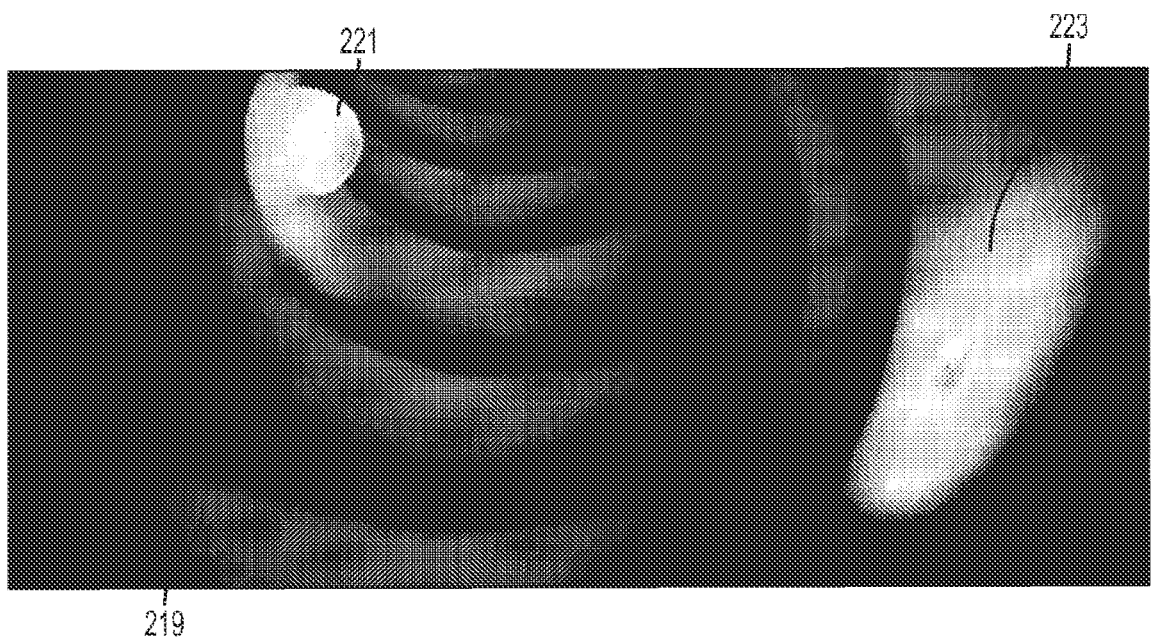
FIG. 2b shows a representative oxygen map overlaid on endoscopic video images.

FIG. 2*a* depicts an embodiment of the present invention wherein the system generates a graphic overlay (205, 211) identifying the location of lesions, including polyp or other abnormalities, or vasculature (203, 209) in subject tissue onto synchronously acquired endoscopic video images 201. The tissue 201 represents colonic tissue, however the endoscopic system can be used to image any biological tissue. FIG. 2*b* shows an embodiment of the overlay that presents a map of tissue oxygenation (221, 233), which may appear as a false color semi-transparent overlay 219. In other embodiments, other physiological properties may be displayed along with corresponding anatomical imaging. The system is capable of measuring oxygenation through some visual occlusions such as tissue folds, and is capable of localizing lesions typically hidden behind folds 215 or other obstructions. In one embodiment, the system automatically identifies suspect lesions (203, 209) and generates an overlay that highlights suspicious lesions (205, 211) based on resolved oxygenation (221, 223); the overlay may be one of a generic mark (e.g., a crosshair or box such as in FIG. 2*a*), an outline of the lesion, a probability map, and an overlaid oxygen map as shown in FIG. 2*b*. This identification process may incorporate statistical data in assessing whether the measurements indicate the presence of a non-cancerous, pre-cancerous, or cancerous lesion, or other features of interest. The colon lesions can include, but are not limited to, inflammatory, hyperplastic, adenomatous or tubulovillous polyps. It may further incorporate a level of certainty associated with the assessment. The overlaid oxygen map (or other property) may be registered to the endoscope video so as to ensure alignment. In a further embodiment, the features in the endoscope video are tracked through an interactively updated image-based registration process, so as to maintain the image overlay even if the secondary imaging system/camera system is removed (such as to insert an instrument down the working channel). In one embodiment a sensor such as electromagnetic tracking sensor or an inertial measurement sensor is used to monitor the absolute position or relative change in position of the imaging system. The system may be configured to automatically detect a lesion or other physiologic structure based on oxygenation, and may be rendered in false colors (i.e., color map) representing measurements in live oxygen map video feeds or static images. The system may be configured to detect and localize vasculature, and in one configuration use this information to guide a surgical intervention. Such guidance may be used to help localize a vessel, and may be used to avoid unintentional damage to the vessel.

Figure 3:
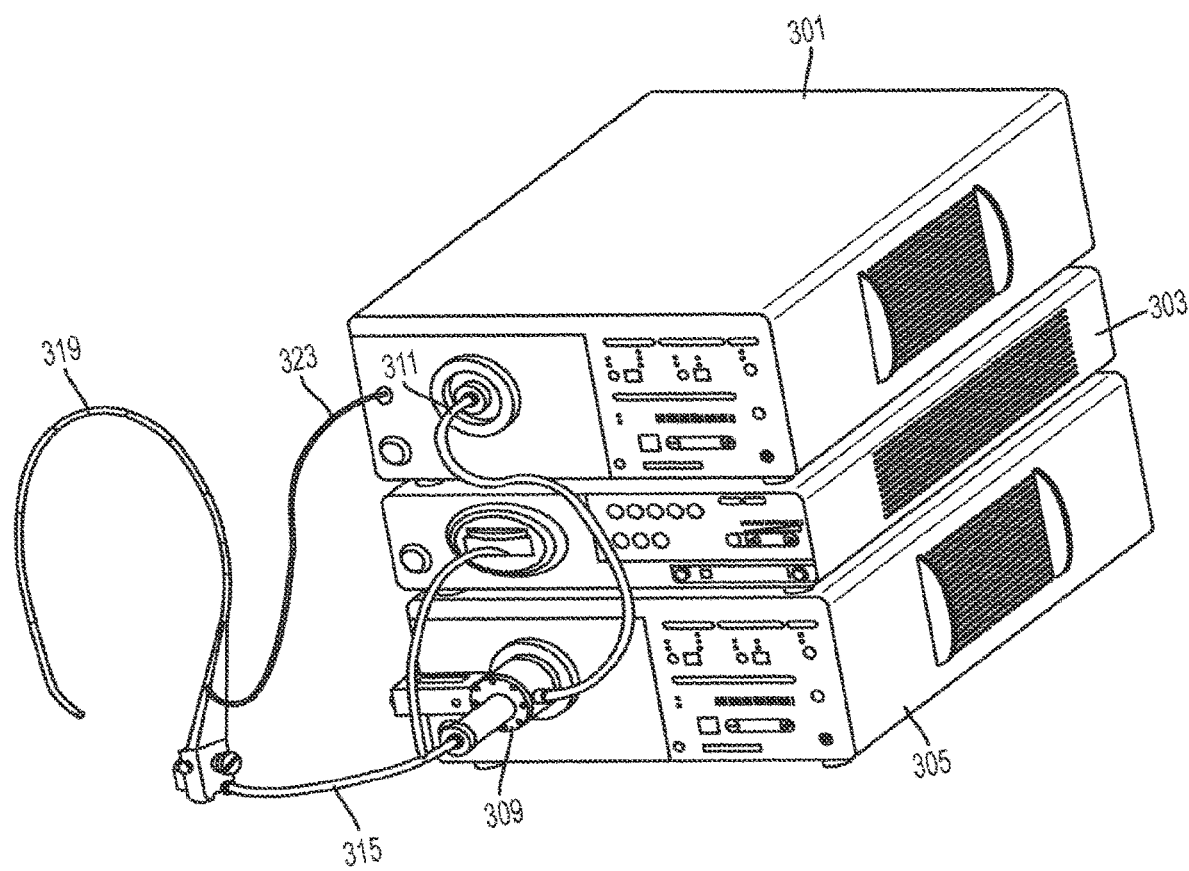
FIG. 3 shows an embodiment where the oxygen mapping system couples with a traditional endoscopic imaging system.

FIG. 3 shows an embodiment of the present invention where the oxygen mapping system includes an oxygen mapping system control unit 301 that couples seamlessly with commercially available endoscope interface units including the control unit 303 and light source 305 (which may be combined or separate components). A coupler 309 in the light path can be used to inject the required modulated light coming from the secondary light source 311 into the existing illumination fiber bundle 315 and pass through irrigation or other connections as necessary through the flexible endoscope 319. If a suspicious lesion is identified the system can allow for exchange of the oxygen mapping camera 323 for another instrument, while retaining/tracking the lesion highlighted on the video monitor. Oxygen mapping can be realized using oxygen dependent quenching of phosphorescence utilizing a systemically injected molecular probe. In one embodiment, the secondary video feed 323 can be used for PLI imaging and may take the form of electrical connections to a microcamera at the distal tip of a catheter. In an alternate embodiment, the secondary video feed 323 may take the form of a coherent fiberoptic bundle directing light to an imaging system inside the oxygen mapping system control unit. The imaging system may be a microcamera (such as a CMOS image sensor), a traditional camera (such as a CMOS or CCD camera unit) or may be an intensified scientific imaging system as further described in this disclosure. In one embodiment, the oxygen mapping system also comprises temperature measurement capabilities. In one configuration, a coherent fiberoptic bundle capable of passing infrared light can be used for thermal imaging; the fiberoptic bundle may be an independent bundle, a multiplexed use of an illumination fiber bundle, or a multiplexed use of the oxygen mapping secondary imaging system's fiber bundle. In an alternate configuration, a discrete point temperature such as a thermocouple can be used to assess the tissue temperature at the imaging site. In a still further configuration, an external sensing system for measuring core body temperature can feed into the PLI system.

Figure 4:
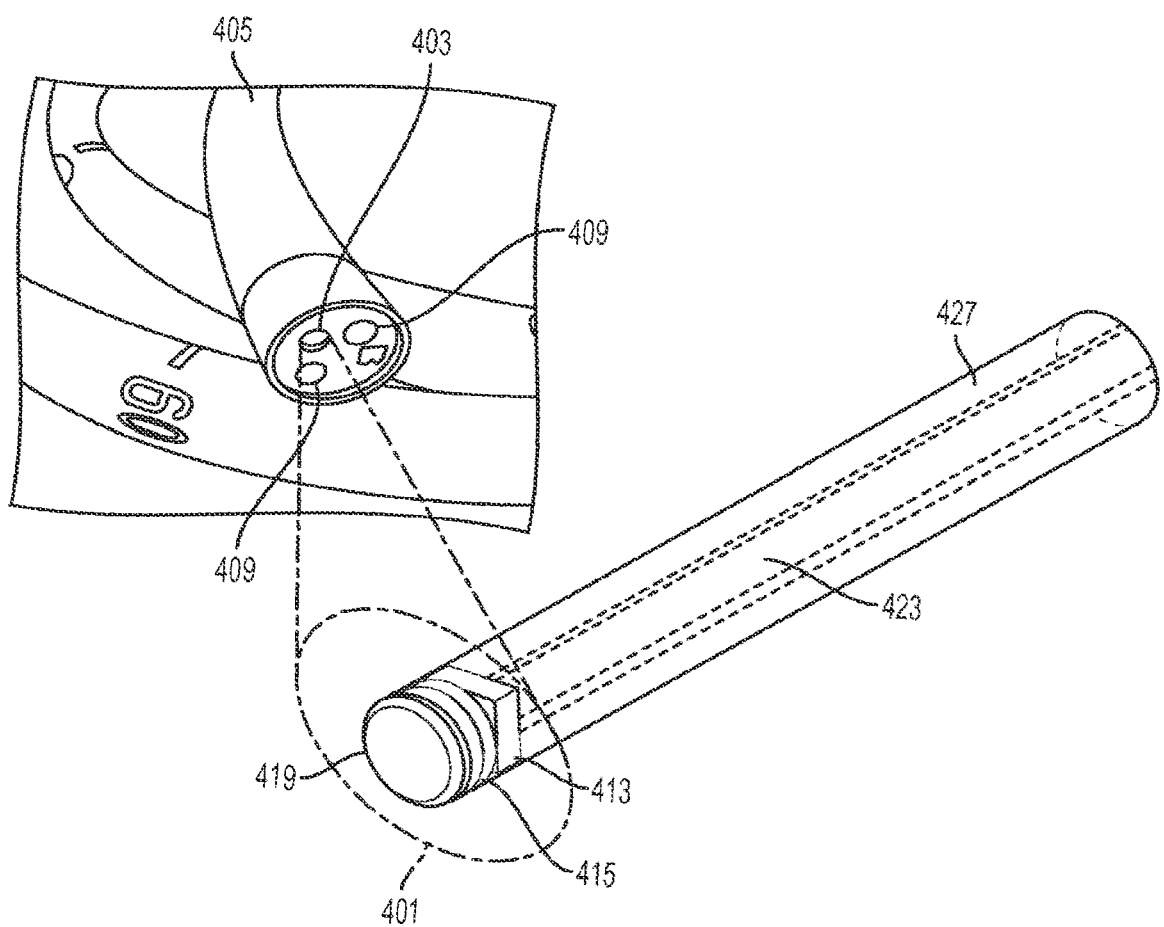
FIG. 4 shows a close-up view of one embodiment of the micro-camera endoscopic imaging system that fits within the instrument channel working port of an endoscope.

FIG. 4 shows a close-up view of one embodiment of the micro-camera endoscope 401 that fits within the instrument channel working port 403 of an endoscopic scope 405 such as a colonoscope. Incident light is emitted through optical fibers 409 or integrated light sources such as LEDs that elicits a phosphorescent, fluorescent, or other light re-emitting response from the target tissue or object. A camera 413, such as a micro CMOS sensor which may include the control circuitry, is placed proximal to an optical filter 415 that removes incident light (long pass filter), leaving the re-emitted light. The sensing approach may be time domain, frequency domain, or an alternate method. Using a time domain method may eliminate the need for, or reduce the required optical density of, the filter 415. A wide angle lens 419 may be used to obtain a wide field of view. Microlenses may be incorporated onto the camera sensor. The camera 413 and lenses 419 may be configured so as to provide an angled view of the tissue. A micro thermal imaging camera may be further incorporated for assessing tissue temperature at the imaging site. The camera may be an independent device, or a combined imager capable of both PLI and temperature mapping. Additional approaches known in the fields for temperature measurement at one or more points may also be incorporated. The camera or cameras pass their data out along cables 423. The secondary imaging system can be contained in a flexible outer sheath 427.

One embodiment of a PLI system based upon either distal imaging (e.g., a microcamera at the tip) or proximal imaging (e.g., fiber bundle to external camera) can provide an ultra-wide view angle. By providing a large view angle, it can be possible to visualize behind objects such as a polyp, tissue fold, stenosis, or anastomosis. The distal end of the imaging system may be able to be actively flexed so as to provide sufficient view to see the rear side of an object. This embodiment may incorporate pre-bent shape memory alloys so as to provide a predefined curved shape when extended. In one embodiment, a cylindrical prism-like device is used to generate a very large angle of refraction and thus a greater than 180 degree view. In another configuration, stacked layers of high index of refraction medium are utilized to create an ultra-wide view angle lens.

In one embodiment of the present invention, a medium can contain fluorescent or phosphorescent oxygen sensing molecular probe. A light source may be a narrow band light source such as an LED or laser, or may be a broadband source such as a white light source. The peak emission wavelength of the narrowband source can be selected to be at or near an absorption peak of the molecular probe in the medium. An optical filter may be used to further restrict incident light to wavelengths in or near the absorption wavelength region of the molecular probe. The molecular probe can re-emit light which then optionally passes through a filter to isolate the emission light from the incident light. A light detector can sense the intensity of received light. In one configuration, a detector can be a single point detector such as a PD, APD, SiPM, or similar device. In an alternate configuration, a detector can be a multi-point detector or image sensor such as a camera or an array of single point detectors. The camera may be CCD, CMOS, or other technology and may be directly at the tissue contacting surface of instrument or optically coupled at a remote location such as through an optical fiber bundle. The array of single point detectors may be PD array, SiPM array, linear CCD or other technology. The light source may be directed over a broad area or precisely directed at a point of interest and scanned. The light detector may be directed over an area or precisely directed and scanned. In one configuration, a processor commands light pulses from a light source and analyzes the time response of the signal received by the detector using time domain signal processing techniques. In an alternate configuration, the processor can command modulated light such as a sinusoidal intensity profile from one or more light source and can analyze the measured signal from the detector to determine the phase lag through frequency domain signal processing techniques. In one configuration the medium can contain a phosphorescent molecular probe. The probe phosphoresces when excited by wavelengths of light in the probe's absorption band(s). The phosphorescent lifetime can be responsive to the oxygen content in the vicinity of the probe due to oxygen's ability to quench the phosphorescence. The relationship between oxygenation and phosphorescent lifetime may follow the Stern-Volmer relationship. Time domain or frequency domain techniques may be used by the signal processor to quantitatively resolve the corresponding oxygen content or concentration in a single location or multiple locations of the tissue. The term "resolve" is intended to be interpreted broadly to mean to calculate, compute, determine, assess, or acquire the solution for oxygen content or concentration in the target tissue. An exemplary implementation of the time domain or frequency domain techniques is disclosed in U.S. Pat. No. 6,701,168, which is incorporated herein by reference in its entirety. Oxygen content may be represented as a number or shown as a map of oxygenation on an instrument or an external display unit. The oxygen content may be used to predict the likelihood of success or failure of the surgical procedure, or guide a surgical procedure. An exemplary implementation of predictive or guidance techniques is disclosed in US Patent Publication No. 2009/0054908 A1. In one embodiment, the instrument is an endoscopic imaging system. In another embodiment, the instrument is an adjunct to a surgical instrument, such as an accessory to a surgical stapler anvil.

Figure 5:
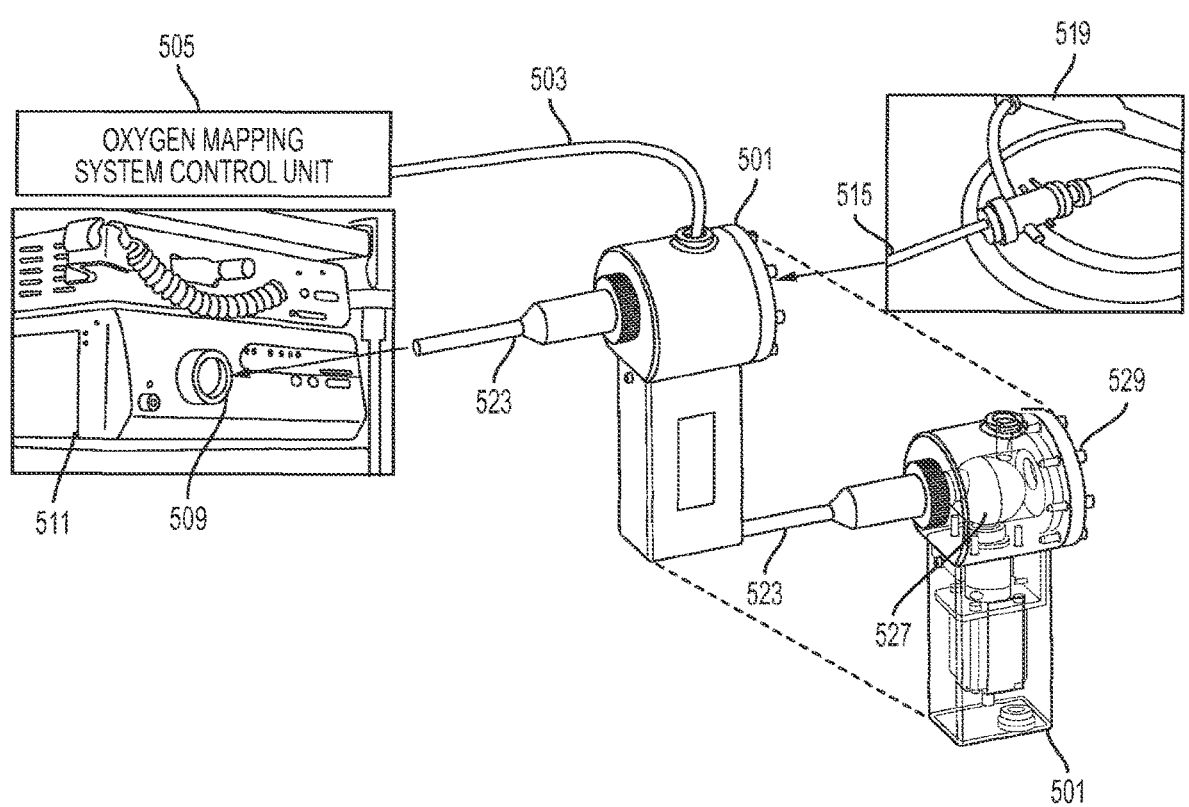
FIG. 5 shows a coupler that enables injection of modulated excitation light from an external control unit into the light path of a traditional endoscopic imaging system.

FIG. 5 demonstrates one embodiment of a coupler 501 that can enable injection of modulated light along an optical path 503 (such as a fiber optic cable) from an external control unit 505 into the light path 509 of an existing endoscope system 511. Light path 509 typically passes white light from a standard endoscopy light source within or associated with endoscope camera controller 511. This enables multiplexing the optical fibers 515 of a traditional endoscope 519 so as to allow white light for traditional video imaging and modulated wave-length specific light for incorporating sensing such as PLI. Light source couple 523 mates with the light port 509 of the endoscopy light source. In one embodiment, a motorized mirror unit 527 can switch between the white light input source 523 and the modulated light source from the oxygen mapping system 503. In an alternate embodiment, solid state or MEMs switching or mirrors such as a DLP-like device may be used. Endoscope coupling 529 can couple to a standard endoscope 519 to pass the combined light output into light path 515.

Figure 6A:
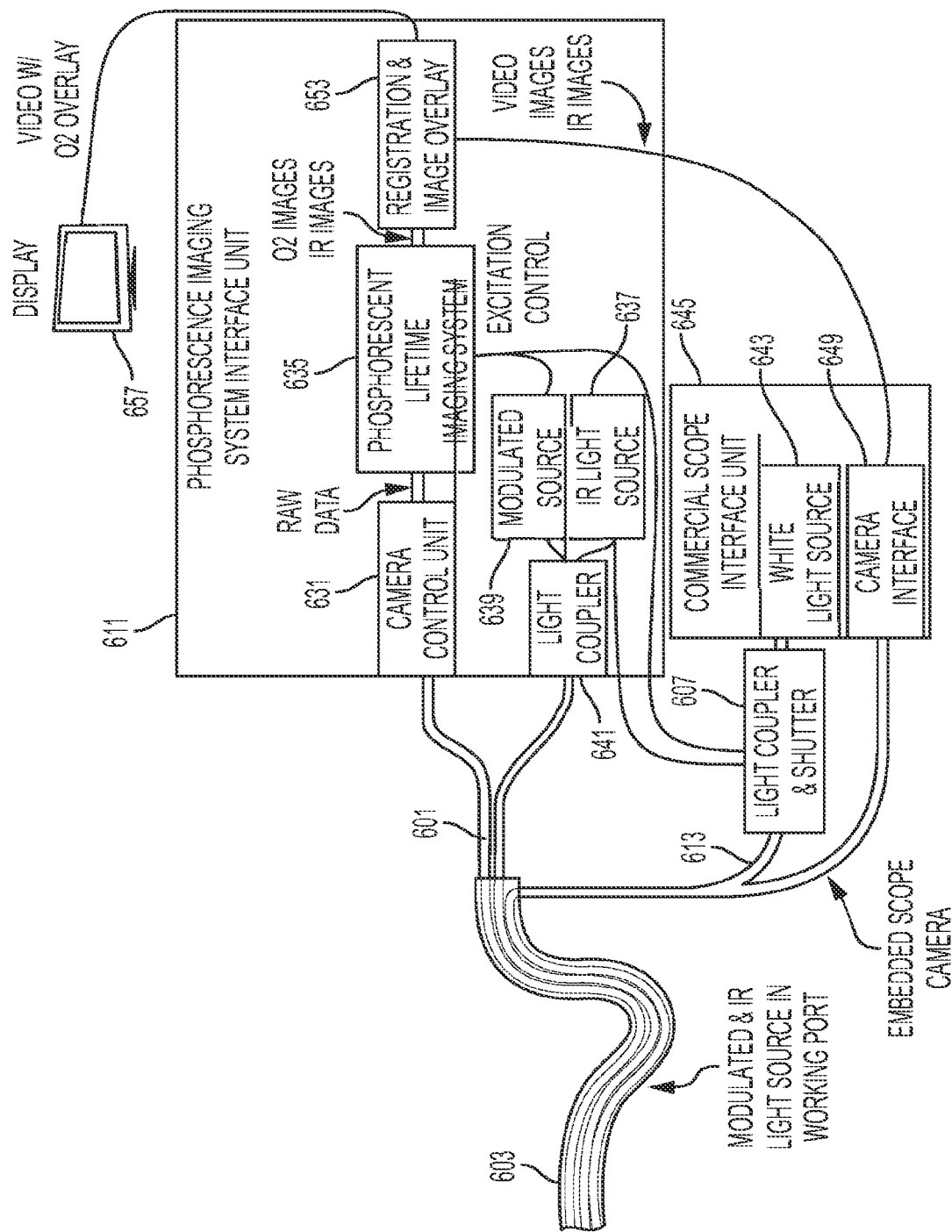
FIG. 6a shows an embodiment wherein a microcamera-based secondary imaging system fits inside the working port of a scope with a dedicated light channel.
Figure 6B:
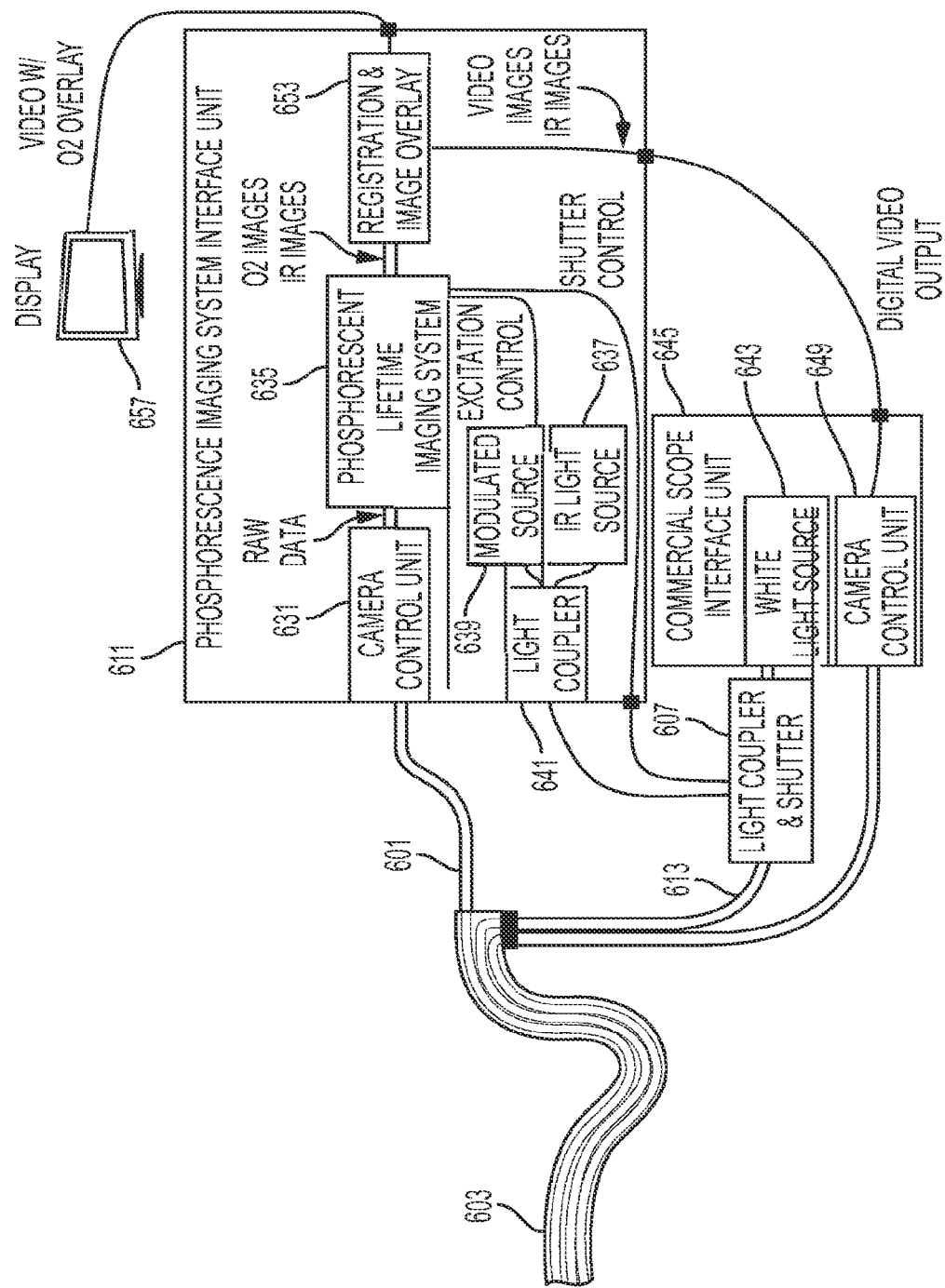
FIG. 6b shows an embodiment wherein a microcamera-based secondary imaging system fits inside the working port of a scope where light is injected along the pre-existing light path.

FIGS. 6a and 6b show embodiments of the system, wherein a microcamera endoscope or fiberoptic scope 601 can fit inside the working port of a traditional commercially available or custom-made scope 603. A light coupler 607 as described in FIG. 5 can inject light from the PLI control unit 611 into the existing scope illumination/light fibers 613. FIG. 6a shows a dedicated light channel for the PLI system and a shutter unit for the scope interface. FIG. 6b shows an alternate embodiment where light is injected along the existing light path 613.

Figure 6C:
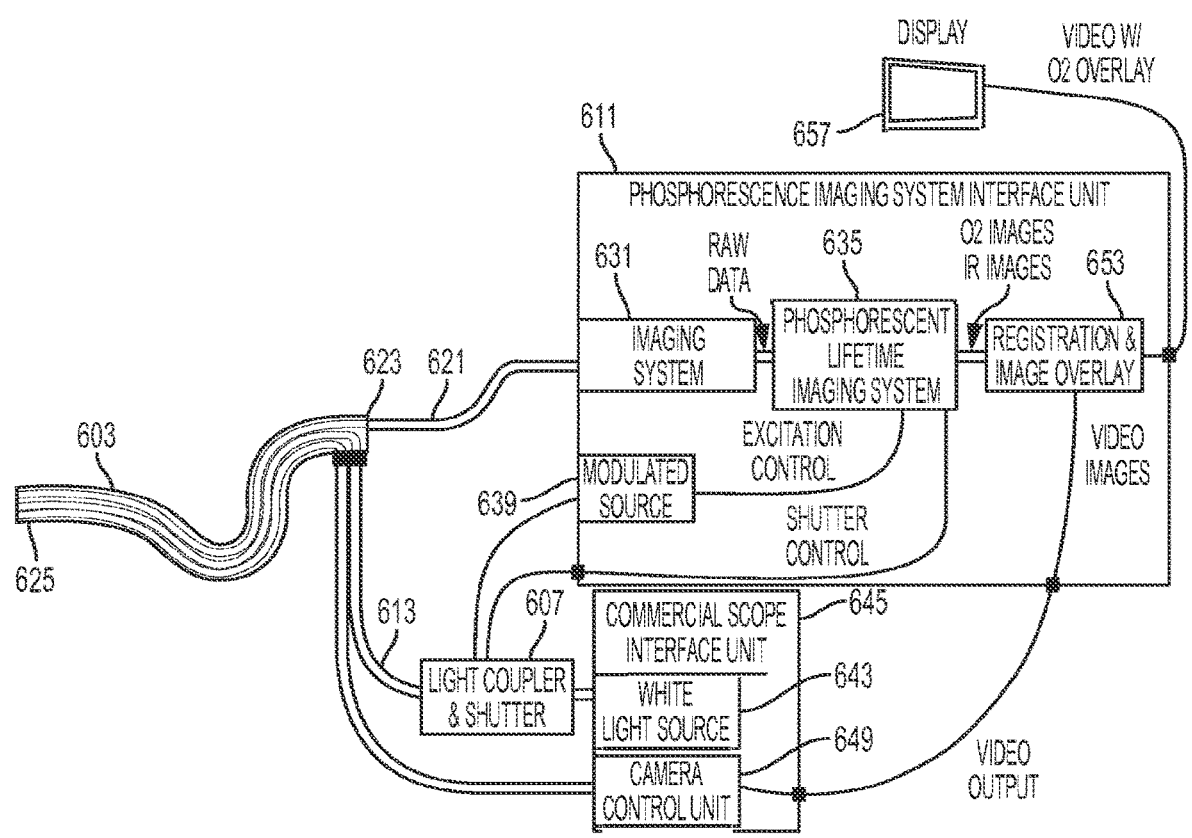
FIG. 6c shows an embodiment wherein a fiberoptic light path of a secondary imaging system fits inside the working port of a scope where light is injected along the pre-existing light path.

FIG. 6c depicts an embodiment of the imaging system wherein a coherent fiberoptic imaging bundle 621 is configured to pass down the working channel/port 623 of an endoscope 603. Endoscope 603 may be a fiber optic imaging flexible endoscope or a flexible endoscope with an integrated microcamera at the distal end 625. The secondary imaging fiber bundle 621 couples with an imaging system 631. In one embodiment, imaging system 631 comprises a gated image intensifier and a sensitive, high-speed camera. The imaging system 631 can be coupled with the phosphorescent lifetime imaging system 635. The PLI system 635 controls camera exposure timing, intensifier gating, and modulation of light source 639. The excitation light from the modulated source 639 may be combined with the visible light source 643 of a traditional, commercially available endoscope controller 645 with coupler 607 and fed into the scope 603 via optical fibers 613. The video feed of the camera control unit 649 from a traditional commercial endoscopic imaging system 645 can transmit endoscopic video images to the PLI system 611. An image processing unit 653 of the PLI system 611 can register the video images from the phosphorescent lifetime imaging and the white light endoscopy imaging. The video images from the commercial endoscope system 645 may be white light video only, or may be a combination of white light images as well as infrared images.

The use of infrared (IR) images based on illumination from a light source 637 (shown in FIG. 6a and FIG. 6b, which may also be applied to the embodiment described in FIG. 6c) fed into a coupler 641 along with modulated light 639 can enable common features to be visible in both images captured by the camera unit 649 and imager 631 to assist in registration. A visual output of the PLI system 611 can be displayed on an internal or external display 657, and may incorporate teachings described in FIG. 2a and FIG. 2b. Note that the detailed description provided for FIG. 6c also applies to FIG. 6a, FIG. 6b, and other embodiments of the present invention.

Figure 7A:
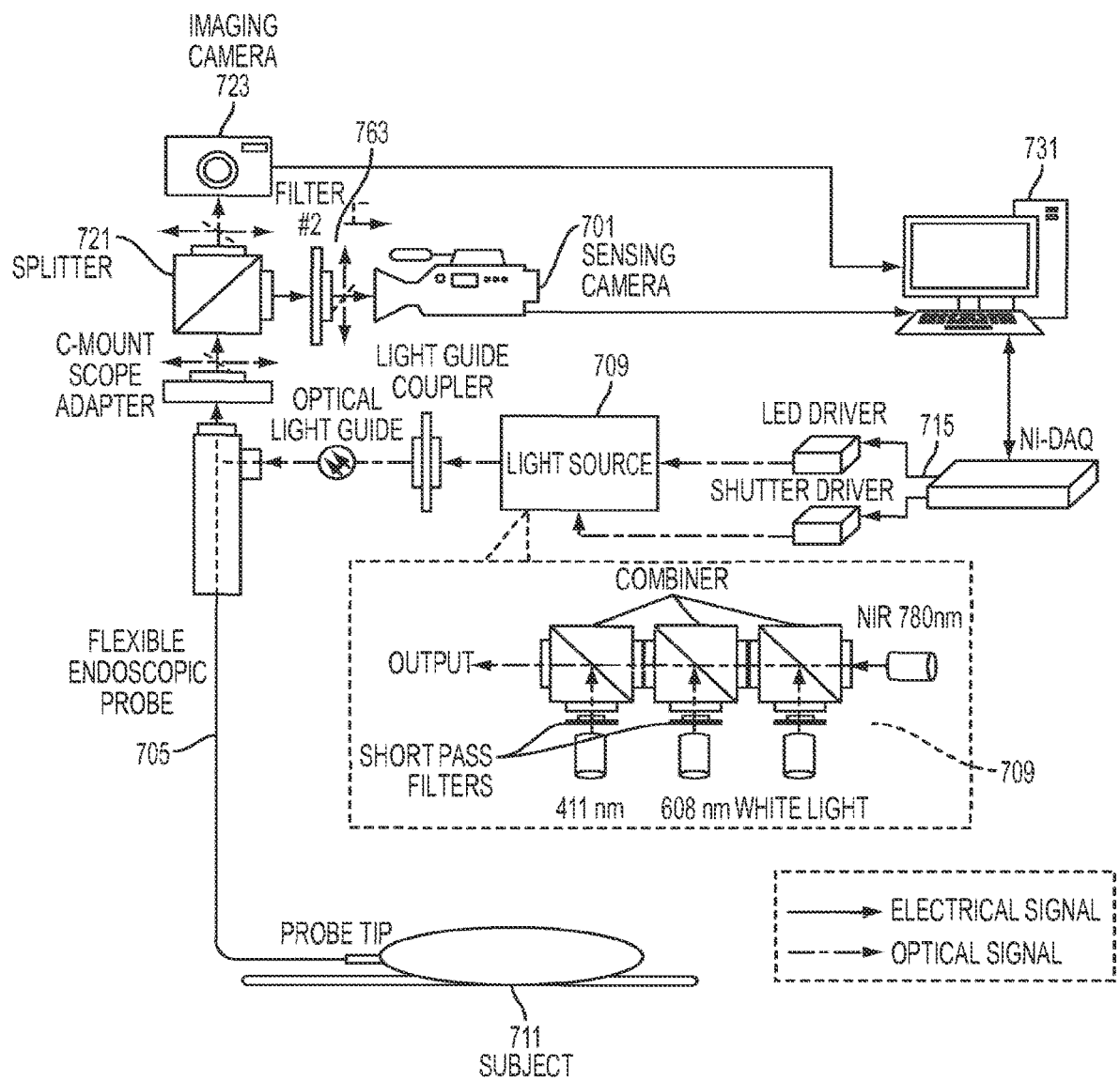
FIG. 7a shows a schematic drawing of one embodiment of the present invention wherein an external sensing camera system is used for generating measurements.
Figure 7B:
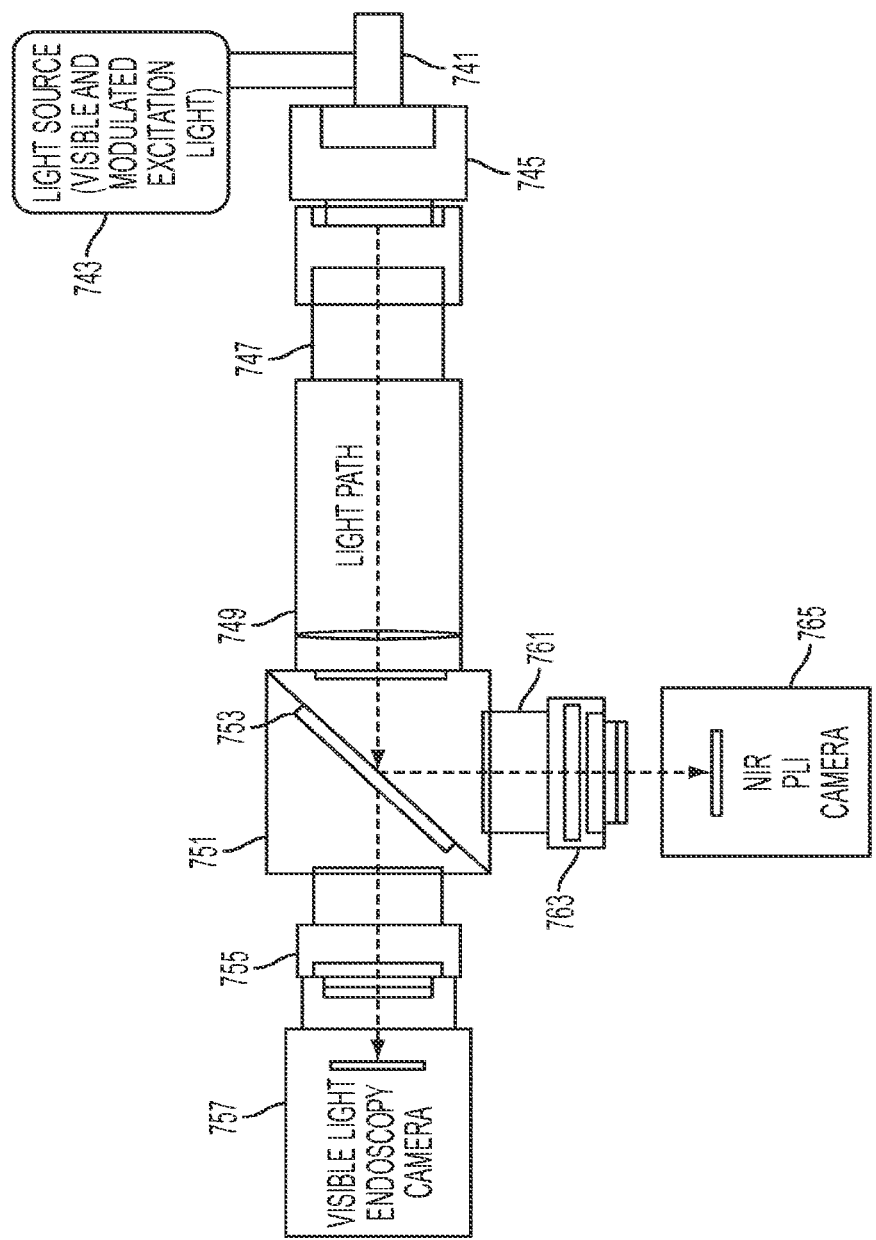
FIG. 7b shows a schematic of one embodiment of the oxygen mapping system configured for coupling with an endoscope.
Figure 7C:
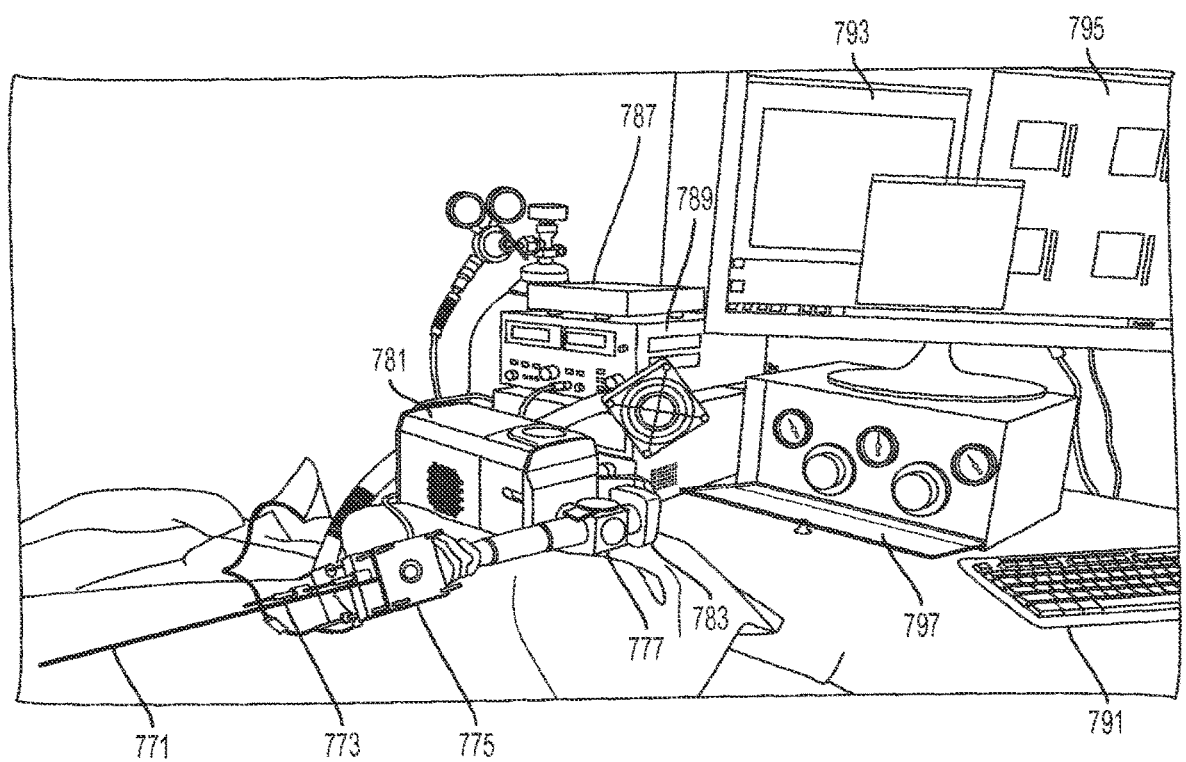
FIG. 7c shows a representative oxygen mapping system configured for small animal trails with a rigid endoscope.

FIG. 7a shows a schematic drawing of one embodiment of the present invention wherein an external sensing camera system 701 can be used for generating measurements. The system may couple directly to a lens, such as for external imaging or open surgical procedures, or it may couple to a rigid or flexible endoscope 705. In one embodiment, the subject can be systemically injected with the oxygen-dependent phosphorescent probe and is then imaged with the system to obtain oxygen maps as well as video images of subject tissue. A light source 709 is used to illuminate and excite the probe in the subject's tissue 711; alternatively fluorescence or phosphorescence of the tissue itself may be detected by direct illumination with or without a molecular probe. This light source 709 may include multiple wavelengths for exciting different molecular probes, different absorption peaks of the molecular probe(s), and for varying light penetration depth (representative wavelengths shown in FIG. 7a are not intended to be exclusive of other wavelengths). Discrete wavelengths as well as broadband sources may be used. Light sources may be LEDs, Lasers, or other sources. The sources may be modulated by a light control system 715 to enable time domain, frequency domain, or other sensing techniques. A splitter 721 can be used to direct the light between an imaging camera 723 (such as a visible light camera) to obtain white light endoscopic images, and the sensing camera 701. In one embodiment, the sensing camera is a high speed intensified scientific camera 701. A filter 763 can allow passage of only re-emitted light from the probe, or native tissue to the sensing camera. The splitter 721 may be a beam splitter, an adjustable mirror, or another way to split the light. In one configuration, the light can be split based on wavelength to send re-emitted phosphoresced IR light to the sensing camera while visible light can be directed towards the imaging camera. FIG. 7b shows details of one embodiment of the system. FIG. 7c depicts one embodiment of the system in a preclinical trial. The device may be used clinically in humans, for veterinary applications, or in laboratory scenarios.

In one embodiment, a processor can interface with the sensing camera 701, the imaging camera 723, and the light source 709. In one embodiment, a computing system 731 can be connected to the sensing camera 701, and a processor of the computing system 731 can perform calculations on the collected image data. Calculations may be used to determine and map fluorescent or phosphorescent lifetime, or a related parameter. The processor of the computing system 731 may be a microprocessor and/or a graphics processing unit (GPU). In an alternate configuration, data from the one or more cameras is passed into a field programmable gate array (FPGA), and the FPGA is configured to perform some or all of the data processing such as determining and mapping fluorescent or phosphorescent lifetime, or a related parameter. One embodiment of the current invention incorporates a gated image intensifier coupled to a high speed imaging sensor. The imaging sensor is communicatively coupled to an FPGA. The FPGA controls the imaging (including exposure timing) and the gating of the image intensifier. The FPGA can also control a pulsed or modulated light source. The FPGA can control the timing and image acquisition. The FPGA also performs image processing on the acquired images. In one embodiment, the FPGA determines a map of the phosphorescent or fluorescent lifetime for each measurement cycle. One approach to the calculation is to assess the exponential decay time constant for each pixel. Performing onboard calculation in the FPGA reduces the need for high-speed data transfer, and thus an embodiment may have an output of oxygen or lifetime maps at a frame rate similar to typical endoscopic cameras over a traditional communication channel such as USB, Ethernet, Firewire, standard PC video such as VGA or HDMI, composite video, component video, or similar.

FIG. 7b shows a schematic of one embodiment of the oxygen mapping system configured for coupling with an endoscope 741 which may be rigid or flexible. Light source 743 feeds into the endoscope's illumination port, and may contain white light and modulated/pulsed excitation light. An adapter (such as C-mount endoscope adapter) 745 can couple to lens tubes 747 including focusing optics 749. A splitter box (such as a cube holder) 751 can contain a splitter 753 which may take the form of a wavelength-dependent hot (IR) mirror splitter. Focusing optics including adjustable lens tubes and adapters can couple one output of splitter 751 to a visible light endoscopy camera 757. The other output of the splitter can pass through focusing optics 761 and a longpass or bandpass optical filter 763 to reach the sensing camera 765. The longpass filter can effectively remove incident light allowing passage of only re-emitted light. The wavelength selectivity of the filters would be dependent on the optical absorption and emission properties of the probe as well as the incident light sources used. The sensing camera can be used for phosphorescent lifetime imaging and may take a form as described in FIG. 7a.

FIG. 7c shows a representative oxygen mapping system configured for small animal trails with a rigid endoscope 771. The scope 771 can also contain or can be coupled with an insufflation channel 773. A multi-wavelength LED light source 775 comprising remotely selectable white light and pulsed/modulated light couples to the illumination port of scope 771. A lens assembly and splitter with filter block 777 (as described in FIG. 7b) couples the scope 771 to the sensing imaging systems 781 and the visible light imaging system 783. In this embodiment, sensing imaging system 781 is an IR-sensitive intensified camera with high-speed gating. A control unit such as a data acquisition system (DAQ) 787 provides for illumination waveform and camera sync control, and may be coupled to a control computer 791. The illumination of light source 775 can be controlled by the modulated light driver 789. The term modulated light can refer to pulsed light in the case of time domain approaches and sinusoidal input in the case of frequency domain approaches. A display of computer 791 can show the white light video endoscope output 793 and the calculated oxygen and/or phosphorescent lifetime map 795. For experimental evaluation, a gas mixer 797 enables control of the subject's inspired O2 concentration.

Figure 8:
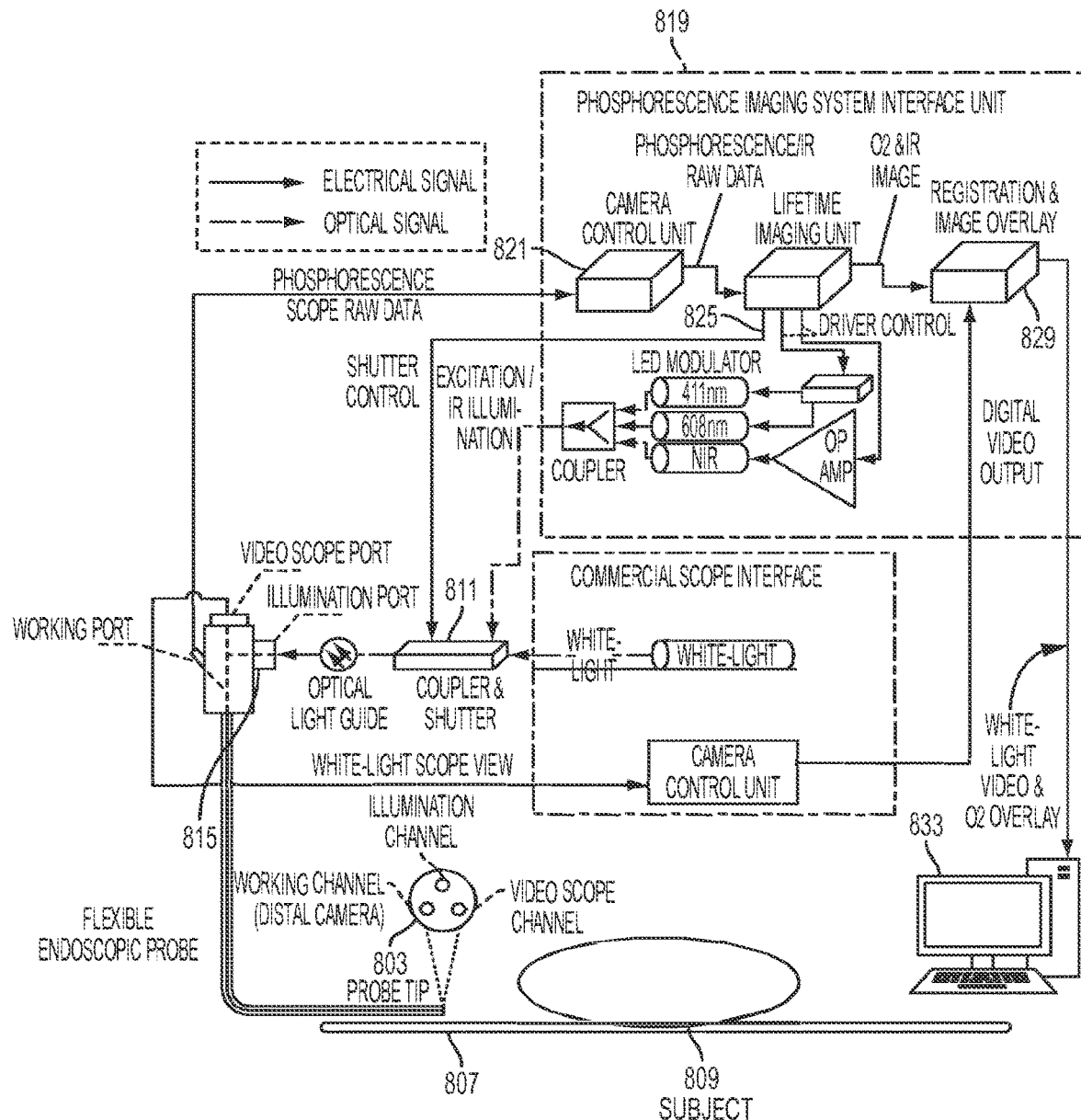
FIG. 8 depicts an embodiment of the system wherein a microcamera device passes through the working channel instrument port of an endoscope.

FIG. 8 depicts an embodiment of the system wherein a microcamera device 803 passes through the working channel instrument port of an endoscope to its distal tip 807 to image a subject tissue 809. This embodiment can be compatible with coupling to both fiber and integrated video scopes. This embodiment can operate similarly to that of FIG. 7a except that the camera 803 can be located at the distal tip 807 of the scope. The depicted system shows a phosphorescent lifetime imaging control system connected to the microcamera and a light coupler 811 for injecting light into the illumination port 815 of the scope. The PLI control system 819 can control the camera controller 821, light source 825, and map generation functionality 829. In one embodiment, it can also acquire visible light images from an external camera unit or another source, registers a map of tissue oxygenation or a proxy thereof to the video image, and displays the tissue oxygenation or other information through an augmented reality image overlay.

Figure 9:
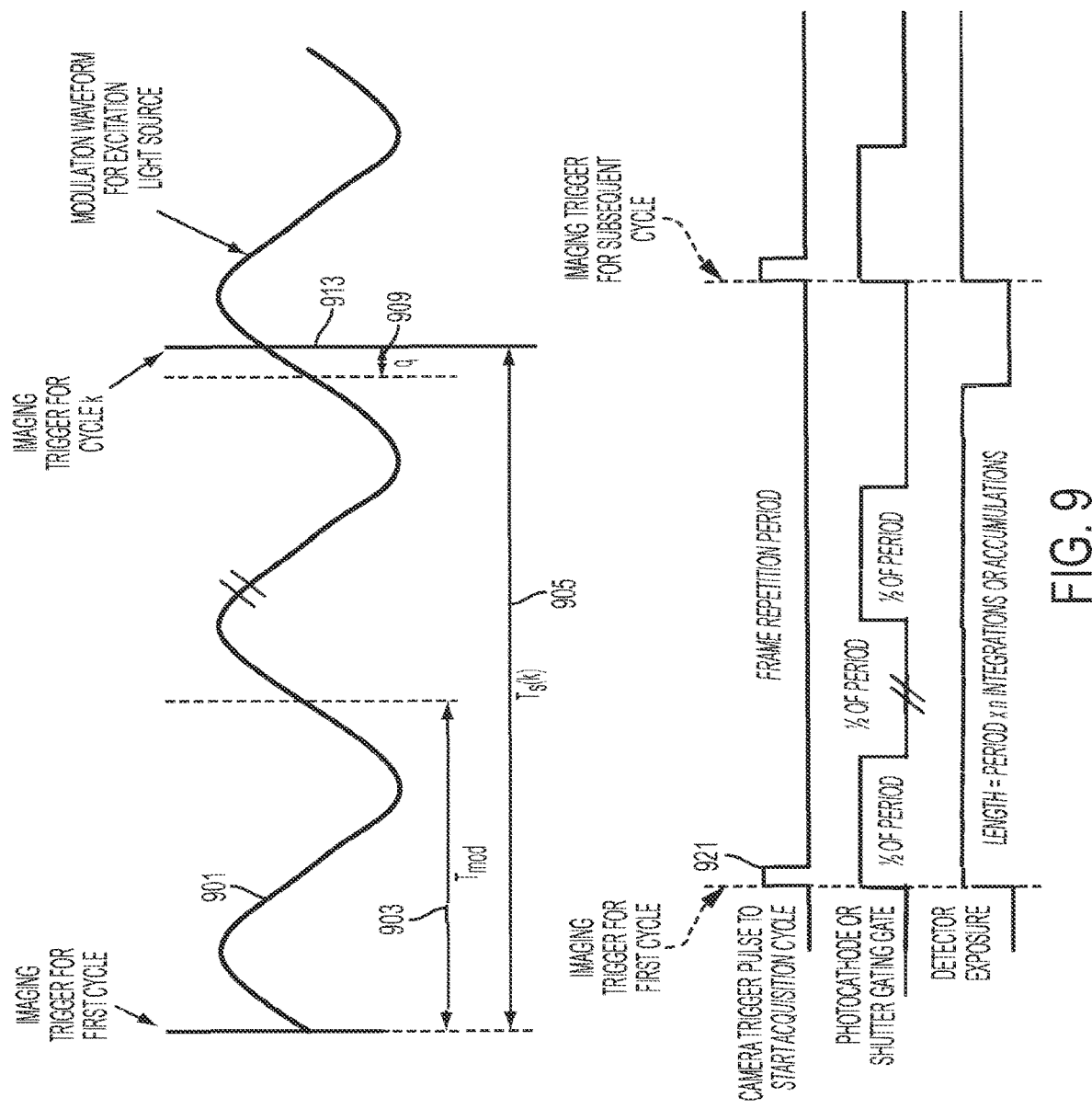
FIG. 9 shows a timing diagram of one embodiment of the sensing system using a frequency domain approach.

FIG. 9 shows an exemplary timing diagram of one embodiment of the sensing system. The figure depicts a frequency domain approach to sensing wherein excitation light is modulated 901 at a frequency with a period Tmod=1/fmod identified as 903 and the system acquires timed images during the repeated periods Ts identified as 905. Ts is defined as: Ts(k)=k*N*Tmod+k*dq for each increment k, where: k=sample number (starting at 0), N=number of periods between sampling (based on camera frame rate), Tmod=period length of excitation modulation sine wave (1/fmod), dq=increment along period for each subsequent sample (equivalent to sampling interval), and q=k*dq=offset from start of period at the current cycle to trigger sampling. The light modulation waveform (upper plot) is made up of a sine wave 901 with frequency fmod for the number of samples desired*N. Each period is staggered by a small amount q identified as 909 to sweep the imaging trigger 913 through the full range of the periodic response. The camera triggering waveform 921 (lower plot) is made up of a pulse train with rising edge at times Ts(k) for each sample k. Multiple accumulation or integrations may be performed by synchronizing the shutter or gate with a portion of the period. This portion can be shifted incrementally to acquire the whole waveform. The phase lag induced in the waveform can then be related to oxygenation. Multiple frequencies may be used to enable more robust measurements, assist in removing incident light that made it through the filter, or determine an oxygenation spectrum. In an alternate embodiment, a time varying frequency such as a linear chirp signal is used to excite the probe to obtain information from a large number of frequencies. The acquisition may be taken sequentially over multiple repetitions of the period or it may be acquired with a high speed camera unit. Scanning or binning of camera sensor pixels may be used to obtain fast imaging of a small subset of the field of view. In another embodiment, a similar approach may be used for time domain measurements. In this approach, multiple points along the optical response decay after an excitation pulse are read out over a series of repeated excitations at a time varying phase delay. Included is an approach for reduced sample rate or frame rate requirements through synchronized, gated imaging of multiple sequential periods. A further approach provides for where multiple acquisitions or accumulations for a given period may be summed together to increase the measured signal or improve the signal to noise ratio (SNR) for that period.

Included in the present invention are algorithms for determining oxygenation based on a frequency domain approaches. The approaches can include a single modulated light excitation frequency, two frequencies to reduce the effect of residual excitation light, or multiple frequencies to resolve the presence and quantity of multiple oxygenation level (i.e., a map of the spectrum of oxygenation). An embodiment includes an approach where frequency is adjusted to maintain an approximately fixed phase. The invention can include an optimization process for determining the optimum frequencies for acquisition. In an embodiment, oxygenation calculation can be based on time domain approaches and maximum entropy approaches. An alternate embodiment can utilize two photon excitation techniques.

The invention includes an approach for time domain oxygenation measurements, wherein temperature measurement information can be incorporated into the conversion from measured phosphorescent lifetime to oxygenation. Further included is an approach for frequency domain oxygenation measurements, wherein temperature measurement information can be incorporated into the conversion from measured phase of the phosphorescent response to oxygenation.

Figure 10A:
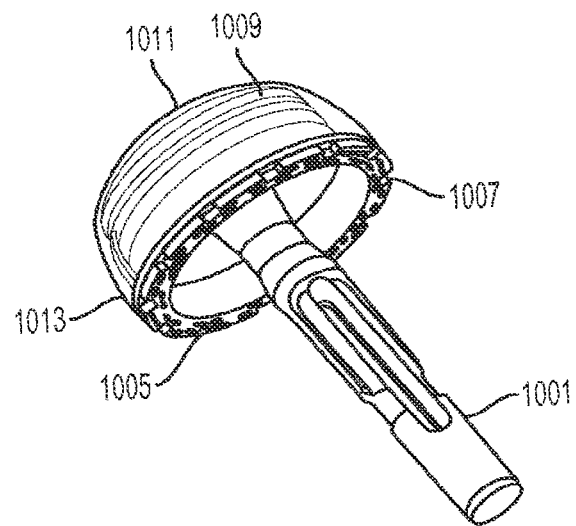
FIG. 10a depicts a surgical stapler anvil with integrated sensors.

FIG. 10a depicts a surgical instrument with integrated sensors. In one embodiment, a surgical stapler anvil 1001 or an adjunct device that couples to the anvil, incorporates sensors. The sensors 1005 on the anvil's working surface 1021 (the surface which forms the staple crimp) may include light emitters and receivers for performing phosphorescent lifetime imaging of tissue on the working surface of the instrument. One embodiment of a sensing anvil 1001 comprises sensor elements 1005 located in cutouts 1007 of anvil face. The sensing anvil contains control electronics coupled to a wireless transceiver 1009 powered by an onboard battery 1011. The sensing componentry is encapsulated inside of a cap 1013.

Figure 10B:
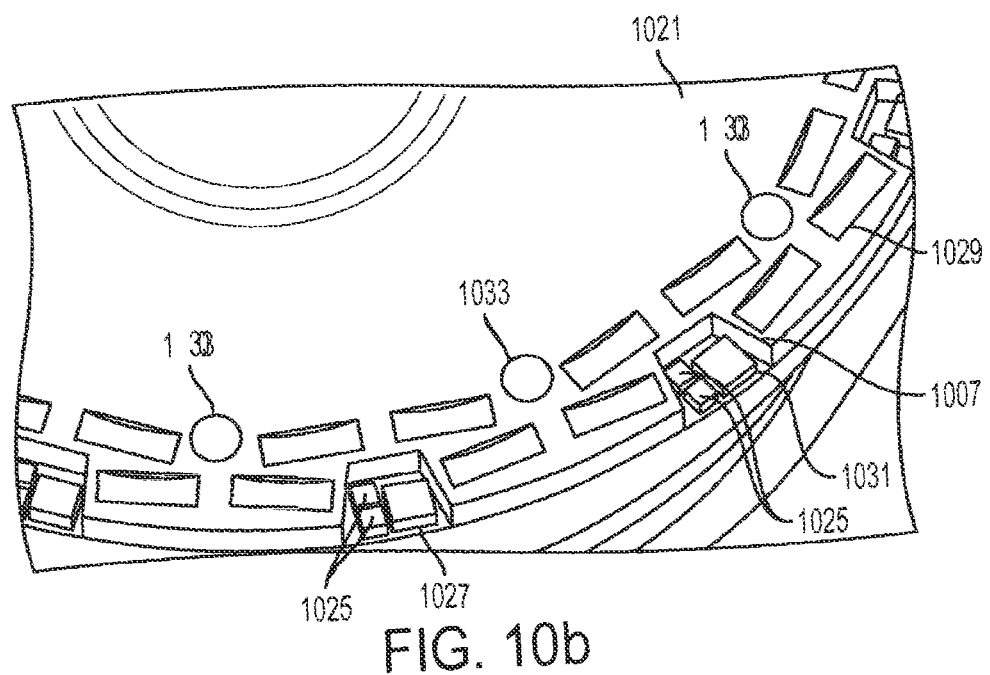
FIG. 10b shows a close-up view of a surgical stapler anvil working surface with integrated sensors.

FIG. 10b shows a close-up view of the anvil working surface 1021. In one configuration LED light sources 1025 and photodiodes 1027 are interleaved in cutouts 1007 between staple forms. Pressure sensors 1031 are also in cutouts 1007 to assess tissue interaction forces. One embodiment of the instrument further comprises one or more temperature sensors 1033, such as a thermocouple or resistance temperature detector (RTD). In one configuration, the temperature sensors may be interleaved between stable forms 1029, distributed circumferentially around the anvil face 1021 and, or located in the cutouts 1007 between the staple forms. In an alternate configuration, a camera can be integrated into the sensing anvil so as to image the tissue through fiberoptics or other light guides. This embodiment can be functionally similar to the microcamera endoscope previously described. In a further alternate embodiment, a sensor can sweep across the device to take measurements at multiple points.

Figure 11A:
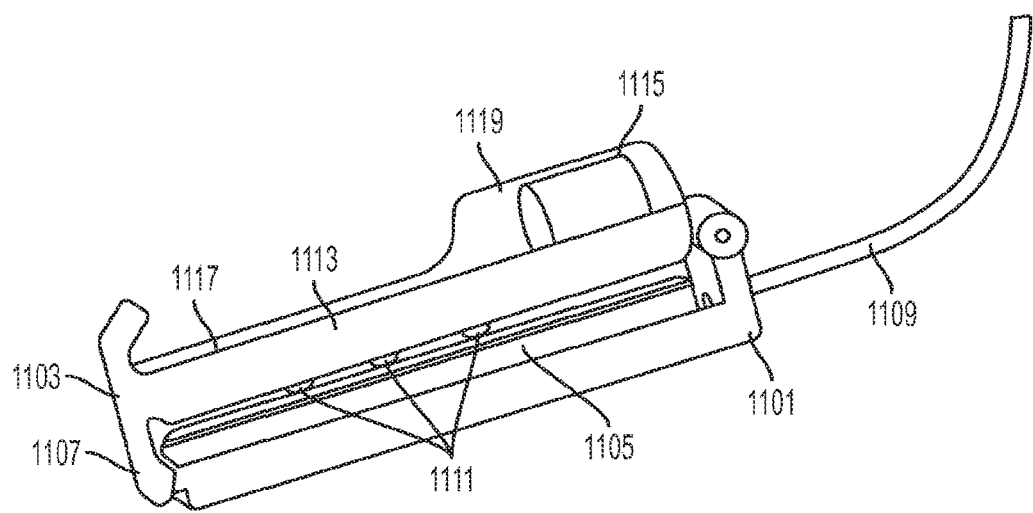
FIG. 11a depicts an embodiment of a medical device with integrated sensors taking the form of a sensing clip.
Figure 11B:
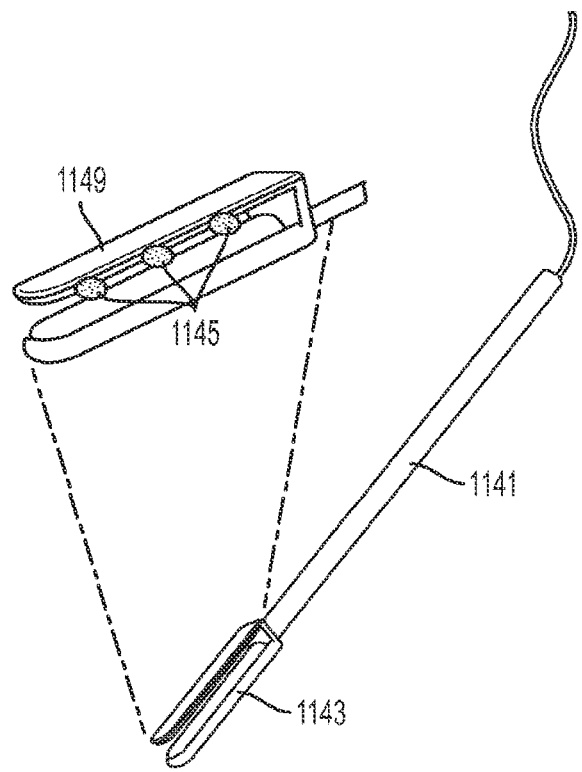
FIG. 11b depicts an embodiment of a medical device with integrated sensors taking the form of a minimally invasive surgical instrument.

FIG. 11a depicts an embodiment of a medical device with integrated sensors taking the form of a sensing clip. In an embodiment, the clip 1101 can be configured to enclose and sense across intestinal tissue. The tissue can be placed between upper surface 1103 and compression surface 1105. A clasp 1107 can hold the sensor closed around the tissue, while a tissue compression bladder or balloon 1105 can compress the tissue to a specified pressure through air or fluid connection 1109. One or more sensors 1111 are positioned along the tissue contacting portion of surface 1103. In one configuration, a linear array of oxygenation sensors can generate a linear 2D map or a 3D array of oxygenations within the tissue. The sensors 1111 can comprise light emitters and receivers for PLI measurement. The sensors can further comprise one or more temperature sensors, that may be associated with each measurement point to enable temperature compensation of the oxygenation measurement. The sensors interface with control electronics (including LED or laser drivers and photodetector amplifiers) and microcontroller or other processor 1113 and can be powered by onboard battery 1115. The system can communicate wirelessly using a wireless transceiver 1117. The sensing system can be enclosed with encapsulant and/or cap 1119. FIG. 11b depicts an embodiment of a medical device with integrated sensors taking the form of a minimally invasive surgical instrument configured as a endoscopic wand 1141. The sensing head 1143 can comprise an array of sensors 1145 that interface with control electronics 1149. The array of sensors on the instrument can comprise one or more of the following: oxygenation sensors, pressure sensors, and temperature sensors.

The present invention includes various sensing surgical instrument and imaging system configurations. One or more sensing surgical instruments may be used in conjunction with an imaging system. In one use of the system, an endoscopic PLI system (such as described in FIG. 3) is used inside the colon, a wand-like device (such as in FIG. 11b) can be used on the outside surface, and an sensing anvil (such as described in FIG. 10a) can be used to assess tissue oxygenation at the site of an anastomosis. The sensors may communicate wirelessly with a base station. This base station may also comprise the PLI imaging system.

Figure 12:
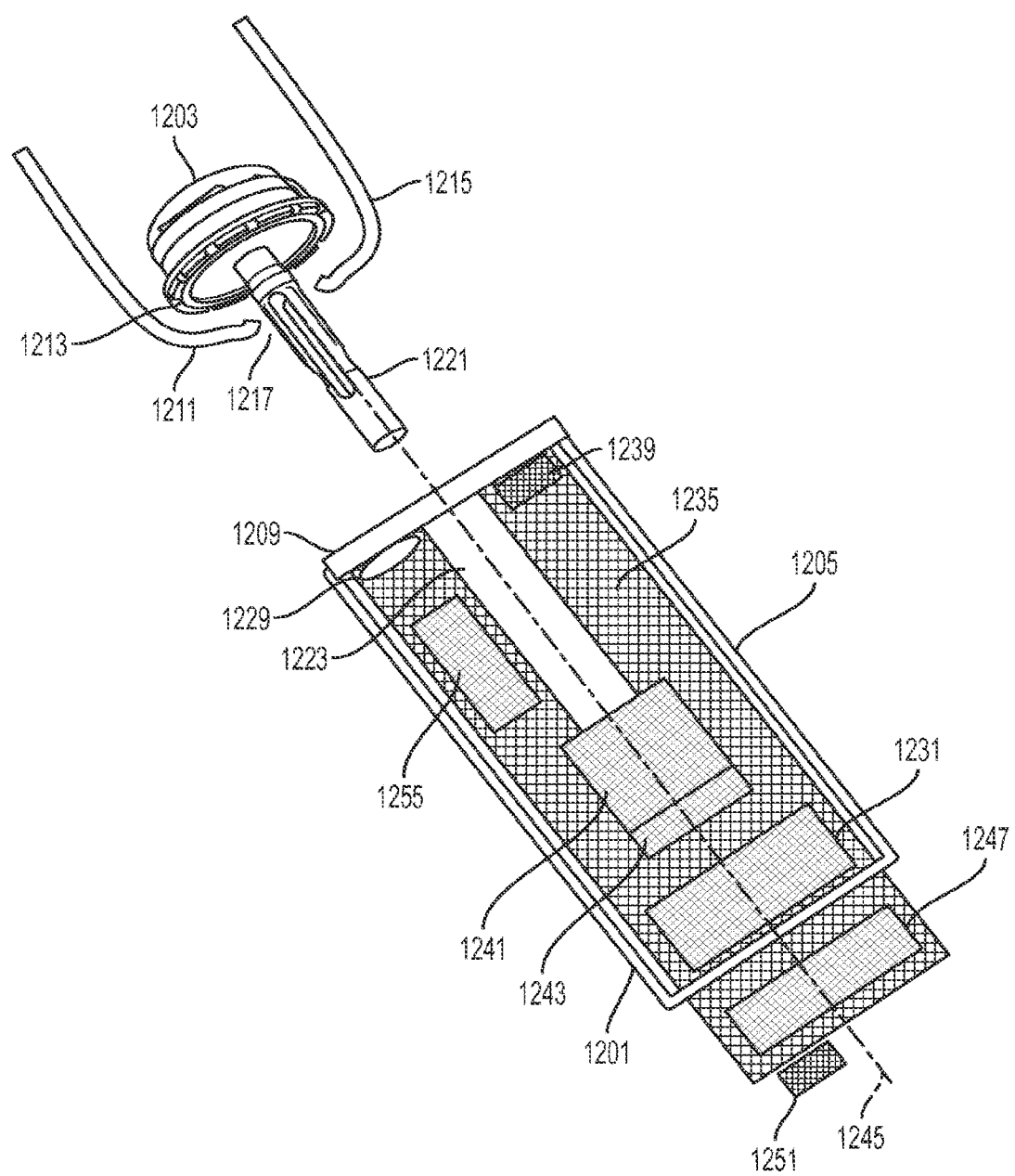
FIG. 12 depicts a cross-sectional view of an embodiment of a self-contained sensing instrument that detachably couples with an anvil of a surgical stapler.

FIG. 12 depicts a cross-sectional view of an embodiment of a medical device 1201 with integrated sensors. This embodiment can contain one or more sensor elements in a self-contained instrument that detachably couples with the anvil 1203 of a surgical stapler. The body 1205 of the instrument 1201 acts as a grip or handle with a tissue contacting surface 1209 that compresses tissue 1211 against the face 1213 of the anvil 1203. In one configuration, tissue 1211 is the site on the proximal end of intestinal tissue such as colon tissue where an anastomosis is to be performed. The head of anvil 1203 can be inserted into intestinal tissue 1215 (e.g., the proximal end of a colorectal anastomosis) and a purse string type closure 1217 can cinch tissue 1211 against the anvil stalk 1221. The anvil stalk 1221 can be inserted into the stalk coupler cavity 1223 to align the anvil with the device 1201. Alternatively, the stalk coupler 1223 (mating member) is a pin (spike) similar to that at the distal end of a circular surgical stapler that inserts into the anvil stalk 1221. In one embodiment, the tissue contacting surface 1209 can act as a sensor window and can be substantially optically clear to allow optical sensing through the sensor window. The tissue contacting surface 1209 may include one or more pressure sensor elements 1229 to allow a processor 1231 to determine tissue compression pressure. The tissue compression pressure may be used to gate oxygenation measurements of the device.

In one embodiment, an internal structure 1235 within the outer housing 1205 can rotate one or more sensor elements 1239 to create a comprehensive reading circumferentially around the anastomosis. In one embodiment, the rotating sensor elements 1239 can comprise at least one light source and one photodetector. The sensors may be used for oximetry, fluorescent imaging, phosphorescent lifetime imaging, or other approaches to optical sensing. In a further embodiment, the light source can be an LED configured to excite a phosphorescent response in an oxygen sensing phosphorescent probe and the photodetector can be a photodiode configured to detect the phosphorescent response of the probe. The rotating sensor element 1239 may also comprise one or more temperature sensors, such as a thermocouple or resistance temperature detector (RTD). The temperature sensors may also be fixed to the body 1205 and non-rotating. A signal processor 1231 can control the one or more light sources and receives and analyzes signals from the photo detector(s). The signal processor 1231 may be used to determine phosphorescent lifetime. In order to obtain a set of readings (i.e., an oxygen map) around the anastomosis tissue 1211, the internal structure 1235 can rotate about axis 1245. In one embodiment the rotation can be by a motor or other rotary actuator 1241, and in another embodiment the internal structure can be manually rotated. An angle sensor 1243 can be used to determine the rotation angle of the internal structure 1235 with respect to the outer housing 1205. In an alternate configuration, a stepper motor can be used and relative rotation angle can be inferred from the motion control signals. In one embodiment the internal structure 1235 is a re-useable, durable instrument, and the outer housing 1205 is disposable and single use. The signal processor 1231 can utilize the optical sensor elements to generate measurements at defined rotation angles, or records the angles at the time of a reading. The signal processor 1231 can reconstruct a map of measurements corresponding to the sensor element positions at the time the readings were taken. In one embodiment, a 360 degree map of tissue oxygenation can be generated for the surface of an intestinal anastomosis by rotating the sensing elements 1239 and taking readings at discrete intervals. In one embodiment, a wireless transceiver 1247 transmits data to a base station and may receive commands from the base station. One or more indicators 1251 may be used to display status of the instrument and/or of the tissue being measured. The sensing instrument 1201 may be powered by an internal battery 1255.

In one embodiment, if a region of tissue is determined to be faulty/abnormal and require attention (e.g., poor oxygenation), the rotating sensing structure can rotate to indicate the faulty position. In a further embodiment, the instrument can align and then illuminate a region of tissue with compromised oxygenation to notify the user. The embodiment described here generally refers to an instrument with at least one sensor element 1239 that couples with another surgical instrument (such as a circular stapler anvil 1203 or housing) and takes one or more sensor readings on the tissue surface 1211. In a more specific configuration, the sensor elements can be configured for PLI and can rotate to determine an oxygen map of the intestinal tissue on the surface of a circular stapler anvil 1213 at the proposed site of an anastomosis 1211. Readings may be taken at a plethora of rotation angles, and may be taken at a plethora of radial distances. The radial placement may be at one or more of: inside the staple forms, at the anvil forms (along the proposed staple line), and outside the staple forms.

The device may be used internal to the body cavity or external to the body cavity. The device may incorporate an injector unit or may work in conjunction with an independent injector unit. The instrument may have an external mark or indicator to facilitate system alignment with an external anatomic structure such as the anti-mesenteric side of the intestine. The external mark or indicator can be mechanically, electrically, or magnetically registered to the internal system electronics to allow for positional awareness of the system with externally aligned anatomy. The instrument may have an integrated mating member 1223 to enable a stable, positive couple (connection) to the anvil or housing. In one embodiment the mating member can take the form of the spike on the stapler to which the anvil is paired, which mates with the anvil stalk. The positive connection can be configured to allow for stability during instrument operation, yet easy release of the anvil once instrument operation is complete. The easy release functionality prevents tissue injury during the uncoupling of the anvil from the instrument. The mating member may be fixed or movably coupled to the instrument. In one embodiment the mating member can be placed along the central axis of the instrument to removably couple to the anvil stalk. The mating member has a central bore that accepts a coaxial rod which allows for travel along the axis. The mating member may be mechanically coupled to the instrument by a constant force spring, or motorized slide such as a linear stage or solenoid to allow for precise control of the tissue interaction forces, such as the contact pressure exerted on the tissue between the anvil and the instrument's tissue contacting surface. The instrument may have integrated interaction force sensors which allow the processor to regulate the interaction force to a set range by actuation of the motorized slide. Similarly the processor may indicate a condition to the end user responsive to the magnitude of the transduced interaction force.

In one configuration of the present invention, the device can be configured to sense oxygenation in multi-layered tissue, or to discriminate oxygenation at different depths of tissue. Using a phosphorescent oxygen sensing probe having multiple absorption wavelengths in a medium, the device can irradiate and excite a subset of the probe injected into the tissue based on the excitation wavelength emitted from the device since the penetration depth in tissue is wavelength-dependent. Oxygenation can be discriminated at two or more depths or layers by exciting the tissue sequentially with multiple emission wavelengths at or near absorption peaks, and determining the corresponding quenched lifetime response. Sensing the deeper values will be a summation of multiple layers, oxygenation at deeper layers can be determined by accounting for the sensed oxygen at shallower layers. In an alternative approach, the phosphorescent decay of various oxygenation levels in heterogeneous luminescence systems (i.e. mixed oxygenations within the tissue sample) can be determined through deconvolution methods to produce a spectrum of oxygenation. In one embodiment of a sensing medical device, a plethora of sinusoidally modulated excitation light outputs are generated (either simultaneously, separately, or combined into a time varying frequency signal such as a chirp) and frequency domain techniques are utilized to determine the spectrum of phase lag of the received signal from an injected phosphorescent medium. By determining the relative contributions of each phase lag, a quantitative spectrum of tissue oxygenation may be generated. In another embodiment, time domain techniques can be utilized to determine the time response of the medium to a pulse of light. Multiple exponential fitting of the decay can be used to generate a quantitative spectrum of tissue oxygenation.

The system described in FIG. 12 teaches a stand-alone sensing instrument for taking circumferential measurements of tissue; the instrument described can rotate so as to allow a maximal number of measurement points with a minimal number of sensing elements. However, it should be understood that a plurality of fixed sensing elements, such as described in FIG. 10*a*, may also be utilized in a similar configuration for the instrument 1201. Also, the methods described herein can be applicable to multiple configurations of a sensing instrument and should not be construed as limited only to the configuration shown in FIG. 12.

Figure 13A:
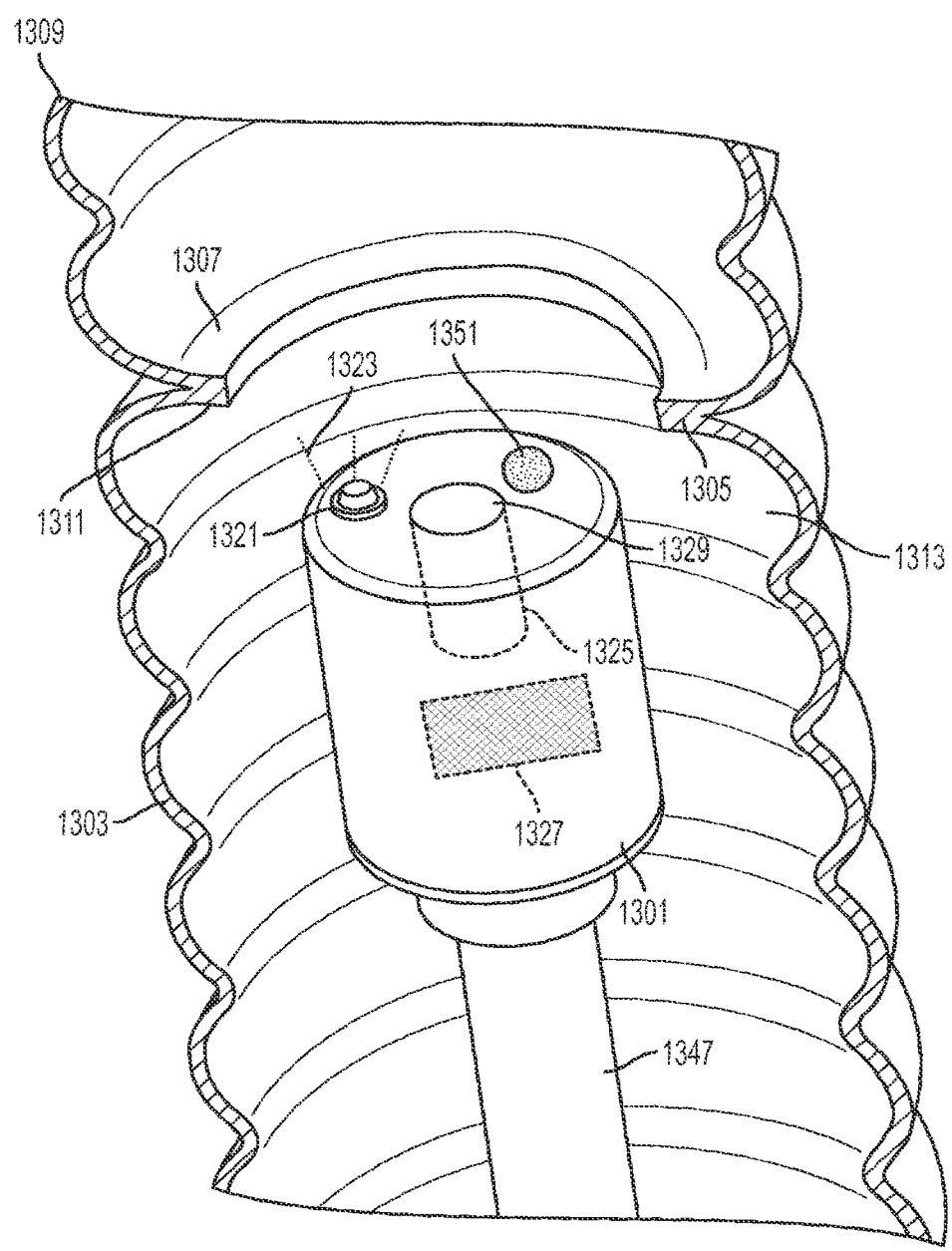
FIG. 13a depicts an embodiment of an imaging system with a light source capable of selectively illuminating a region of tissue.

FIG. 13*a* depicts an embodiment of an imaging system with a light source capable of selectively illuminating a region of tissue. The imaging system 1301 can be endoscopic and in one embodiment can be a flexible endoscope such as a colonoscope that is inserted transanally into colon tissue 1303 at the distal end of an anastomosis junction. The imaging system may be used to image and assess the viability of an anastomosis 1305 (such as through mapping the oxygenation on one or both sides). The imaging system 1301 is configured such that it can be used to image the light-remitted from an injected phosphorescent or fluorescent probe in the anastomosis surface 1307 and the proximal side 1309 of an anastomosis, and the anastomosis surface 1311 and the distal side 1313 of an anastomosis. The imaging system 1301 comprises a light source 1321 that is used to provide illumination 1323 to excite a light re-emitting probe residing in the distal 1311 and/or proximal 1307 tissue of the anastomosis 1305. The excited probe then re-emits a phosphorescent or fluorescent response which is imaged by an imager 1325. Imager 1325 may take the form of a camera embedded in the distal end of imaging system 1301 and coupled to control electronics and/or a signal processor 1327. In an alternate embodiment, imager 1325 is the tip of a coherent fiber optic bundle which conveys light to a remote camera. The light received by imager 1325 is focused through lens 1329, which may also incorporate optical filtering.

Figure 13B:
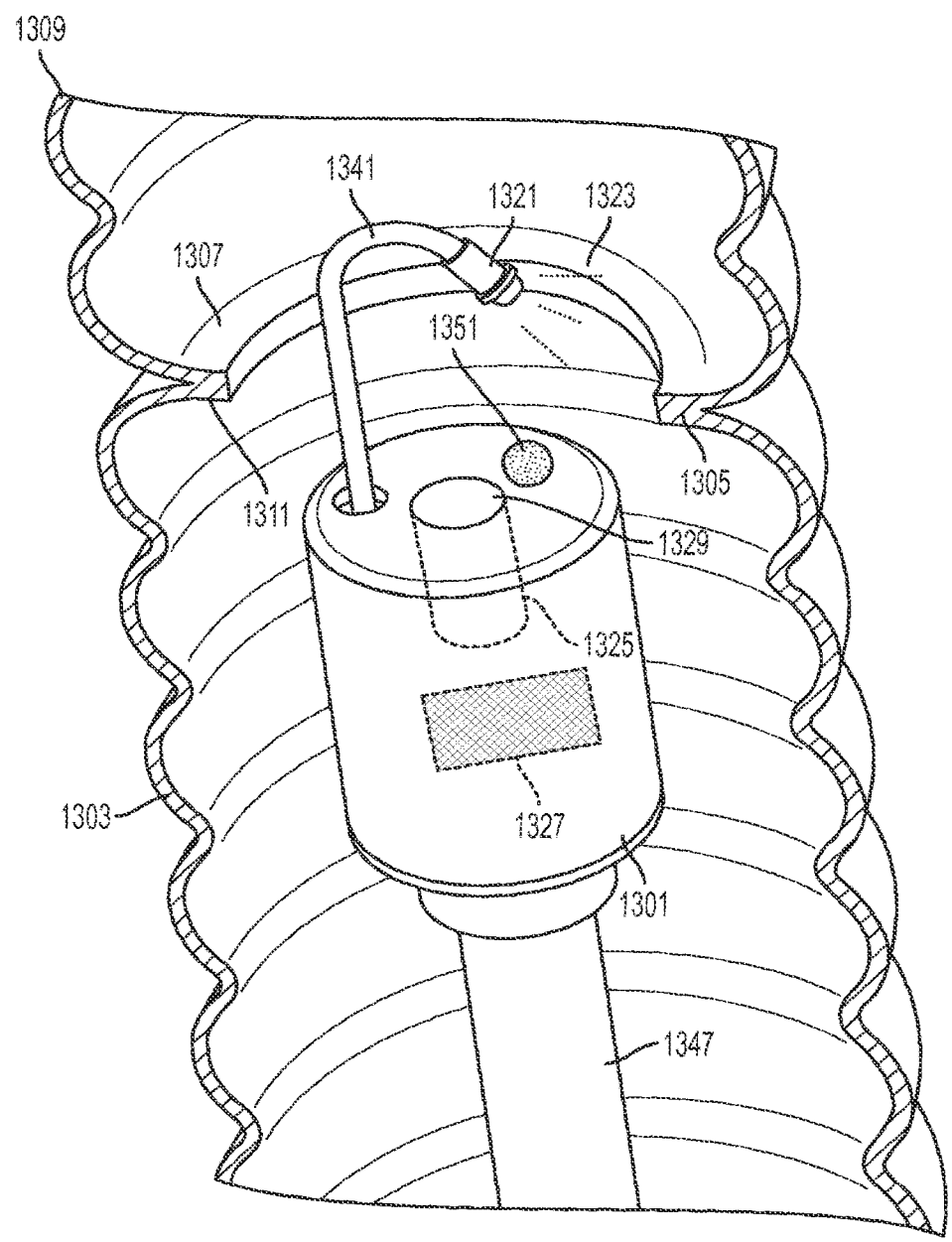
FIG. 13b shows a light source with an extension arm that allows it to extend and rotate.

FIG. 13*b* depicts the imaging system 1301 with a retrograde or retro-view light source extended. The light source 1341 has an extension arm 1341 that allows it to extend and rotate. The arm 1341 may comprise pre-bent Nitinol wire enabling defined curvature by extending and retracting the wire. In one embodiment, the light source is configured to provide both forward (as shown in FIG. 13*a*) and retrograde (as shown in FIG. 13*b*) illumination of a tissue location inside a lumen. In a further configuration, the light source is configured to illuminate the proximal 1307 and distal 1311 surfaces of an intestinal anastomosis 1305.

A method of determining and differentiating tissue oxygenation at multiple tissue layers includes: 1) injecting a phosphorescent oxygen-sensitive probe (or other light re-emitting probe) into the tissue locally or systemically, 2) inserting imaging system 1301 at the tip of rigid or flexible shaft 1347 into the lumen of tissue 1323, 3) illuminating the anastomosis on the distal surface 1311 (as shown in FIG. 13*a*) with a light 1323 at an absorption wavelength of the phosphorescent probe that has a shallow penetration depth in tissue (such as blue to UV range that will not significantly penetrate beyond the distal tissue 1311), 4) using the imager 1325 (such as a CCD, CMOS, or fiber bundle to a camera system) to acquire signals, and use an onboard or external signal processor 1327 to generate an oxygen map of the distal surface 1311, 5) extending the light source 1321 along curved arm 1341 (or an additional/alternate light source), 6) illuminating the anastomosis on the proximal surface 1307 (as shown in FIG. 13*b*) with a light 1343 at an absorption wavelength of the phosphorescent probe that again has a shallow penetration depth in tissue (blue to UV range), and 7) using the imager (such as a CCD, CMOS, or fiber bundle to a camera system) to acquire signals and use an onboard or external signal processor to generate an oxygen map of the proximal surface. The described method enables measurement of tissue oxygenation at a shallow depth of approximately the thickness of the intestinal wall, thus by illuminating from the proximal side, only (or substantially only) the probe in the proximal side is excited. When illuminated from the distal side, only (or substantially only) the probe in the distal side is excited. The phosphorescent response is in the red to IR range and will penetrate through the tissue on either or both sides to the imager. In an alternate embodiment, the light source 1321 contains emitters for at least two wavelengths. One wavelength is at an absorption peak of the probe that has poor tissue penetration and is used to image only the distal side, and another wavelength is at an absorption peak of the probe that has high tissue penetration depth and is used to illuminate both layers. By measuring the oxygenation of the distal tissue and the combination of both layers, the signal processor discriminates the distal and proximal layer oxygenations.

The invention described in FIG. 13*a* and FIG. 13*b* may be configured with either an internal imager or an external imager 1325 coupled through a coherent fiber optic bundle. In either case, an image processor 1327, used to generate oxygen maps may be located externally; for the internal camera the signal processing may be onboard, external, or a combination thereof. The light source 1321 may be an electronic emitter located at the instrument tip, or it may be located externally and optically coupled to the instrument tip through fiber optic bundles or other means. The light source may be configured to illuminate either side of an anastomosis so as to discriminate the oxygenation from both the proximal and distal sides. One or more temperature sensors 1351 may be integrated into the imaging system instrument 1301, or temperature may be assessed though fiberoptic coupling to an external thermal imager. The temperature information may be used to compensate for/calibrate the temperature-dependent phosphorescent lifetime to subject tissue oxygenation.

FIG. 13*b* shows a retrograde light source to selectively illuminate a region of tissue. A configuration of the retrograde light source is capable of illuminating the distal or proximal side of an intestinal anastomosis to excite an oxygen sensing molecular probe in only one side at a time. A further configuration where light source comprises a coherent fiber optic bundle capable of transmitting infrared light, and the fiber bundle may be used to both provide illumination of the tissue and to transmit light from the tissue to a thermal imaging system for temperature mapping. The antero/retrograde imaging system may be configured to generate PLI measurements from both the distal and proximal sides of an intestinal anastomosis as described. An embodiment of the system is capable of multi-modality sensing, and in one embodiment incorporates thermal imaging capabilities. In one embodiment, the instrument takes the form of an imaging system with a large field of view configured for generating oxygen maps on the far side of an anastomosis with a forward facing or substantially forward facing camera. The system can be configured with prisms or stacked high index of refraction elements to generate a large field of view. The present invention teaches a method for distinguishing physiologic properties in various layers using an injectable probe and a light source that selectively illuminates the layers. In a further method an antero/retrograde light source selectively illuminates the front or rear surface of a tissue.

Figure 14A:
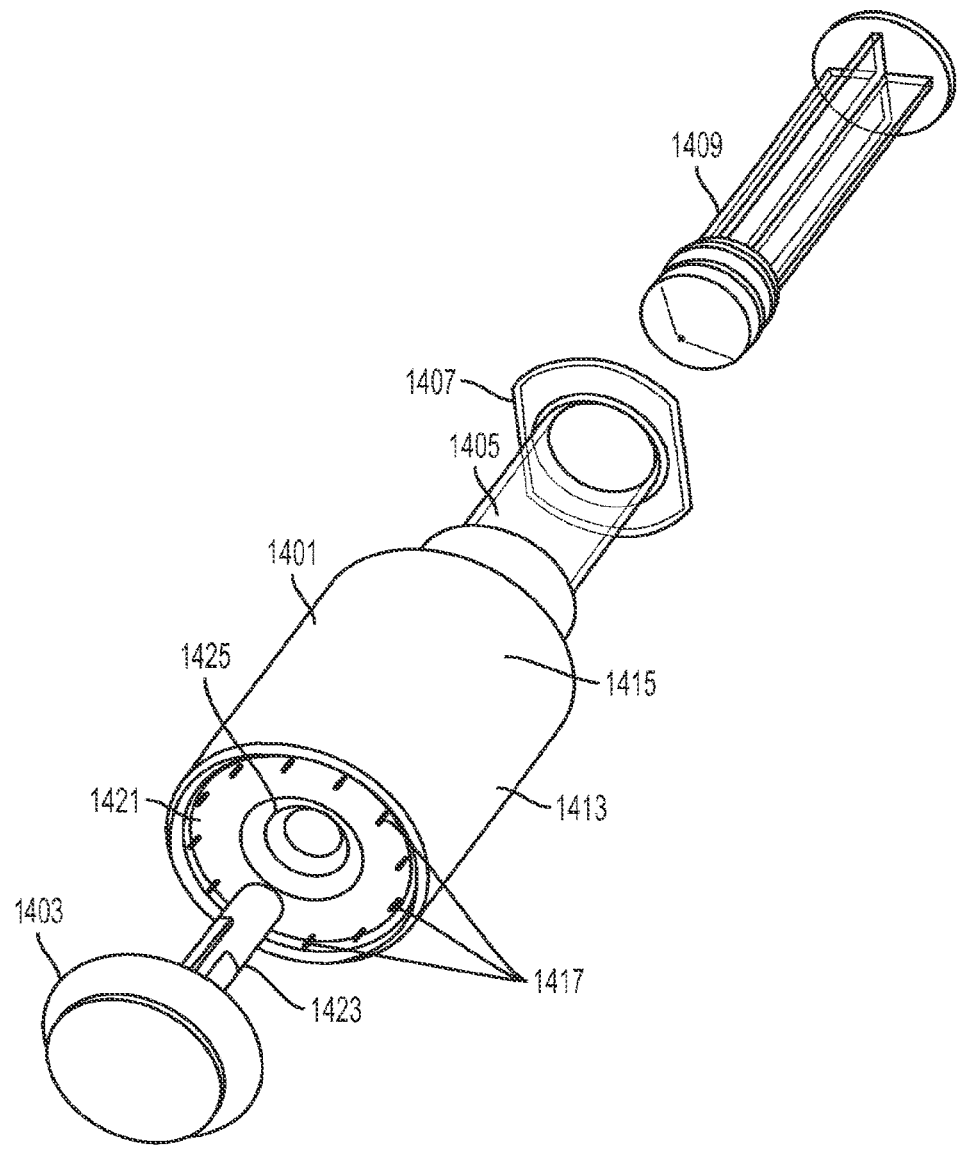
FIG. 14a shows an injector system that couples to a surgical stapler anvil.
Figure 14B:
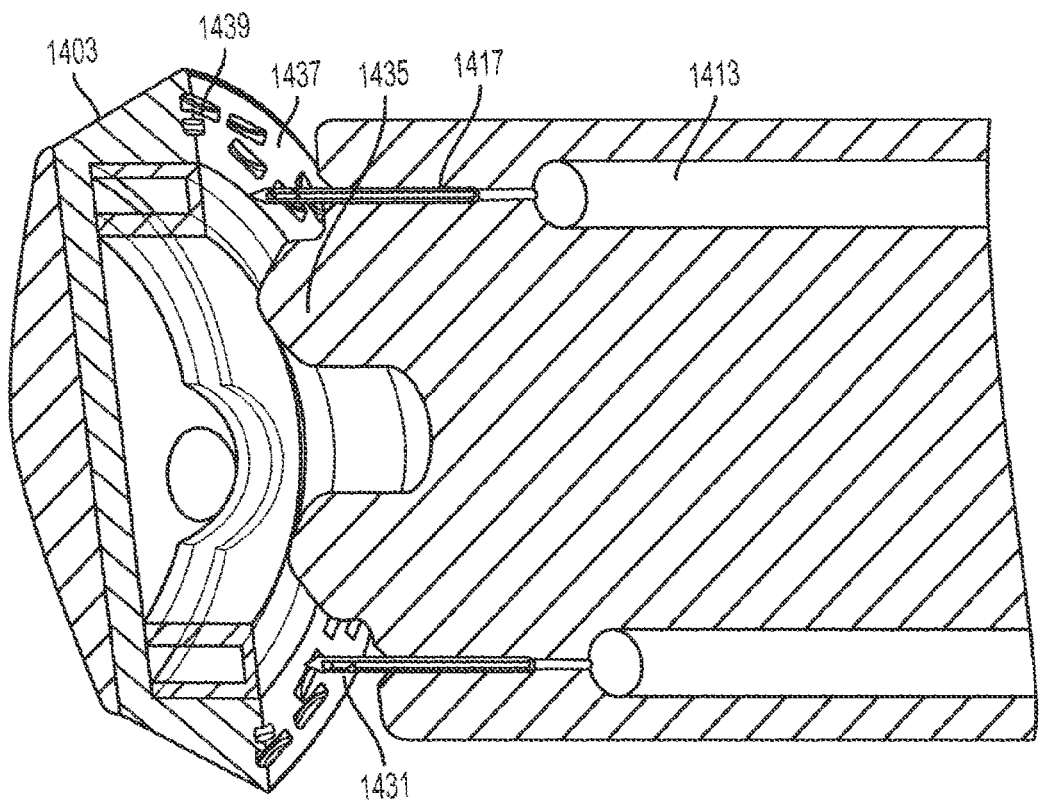
FIG. 14b shows a cross-sectional view of an embodiment of an injector.
Figure 14C:
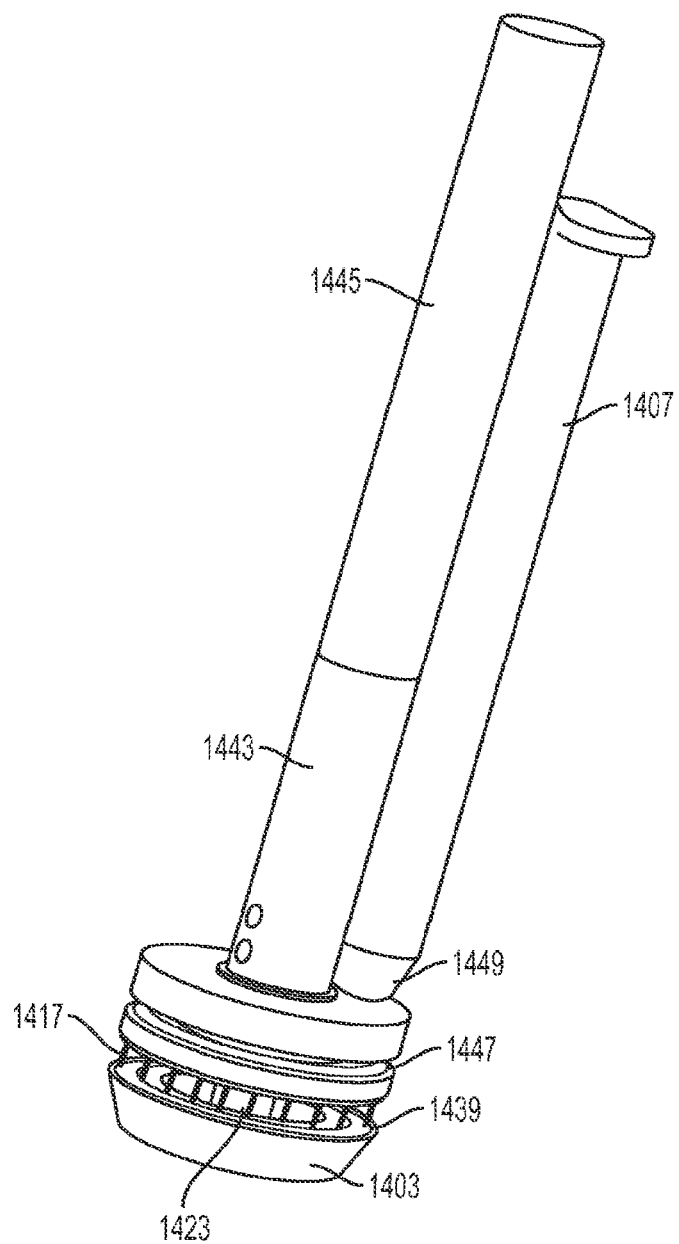
FIG. 14c shows another embodiment of an injector system that couples to a surgical stapler anvil.

FIG. 14*a* shows an injector system 1401 that couples to a surgical stapler anvil 1403. This injector 1401 is used to inject a medium 1405 into intestinal tissue containing the anvil. The handheld device couples with a syringe 1407 filled with the medium 1405. The syringe may be filled with a single injection or multiple doses of medium 1405. The syringe may also be an injector capable of providing multiple metered doses either with a traditional simple plunger 1409, or a manual or powered metered injector. Internal fluid channels 1413 bring the medium 1405 from the syringe 1407 through an internal Luer lock, or slip tip fitting 1415 to the needles 1417. Tissue resides between the handheld device body tissue contacting surface 1421 and the working surface of anvil 1403. The anvil's stalk 1423 connects and is aligned with the instrument 1401 through anvil stalk coupler 1425. In one configuration, the alignment includes keying the anvil stalk's 1423 rotation such that the needle injection points 1417 align with the sensor locations of a sensing version of anvil 1403 as described in FIG. 10*a* and FIG. 10*b*. Small needles 1413 protrude into the tissue. As shown in FIG. 14*b*, the needles 1417 have one or more lateral holes 1431 and a solid tip to direct the medium into the tissue. The tissue contacting surface of the device body 1435 may have a contoured surface to apply different compression to the tissue against the anvil working surface 1437 at different locations to further direct the medium. In one embodiment, the surface is sloped to direct the medium radially outwards from the needles which have holes pointed outwards. In terms of radial placement, needles may be used to inject the medium inside the staple forms 1439, at the staple forms, or outside the staple forms. In one embodiment, the medium may contain a phosphorescent oxygen sensing probe and the oxygenation is detected from a sensing anvil (such as described in FIG. 10*a* and FIG. 10*b*), a standalone device (such as described in FIG. 12), and/or a imaging system (such as described in FIG. 13*a* and FIG. 13*b*). FIG. 14*c* shows an alternate embodiment of the injector unit 1443 that mates with a circular surgical stapler 1403 to inject the medium circumferentially into the tissue around the working surface of the anvil. A handle 1445 attaches to the body of the injector 1443. Syringe 147 connects to fluid channels 1447 through a Luer lock, or slip tip connector 1449. The use of a standard fluid fitting 1449 enables pre-prepared, pre-filled syringed 1407.

Figure 15:
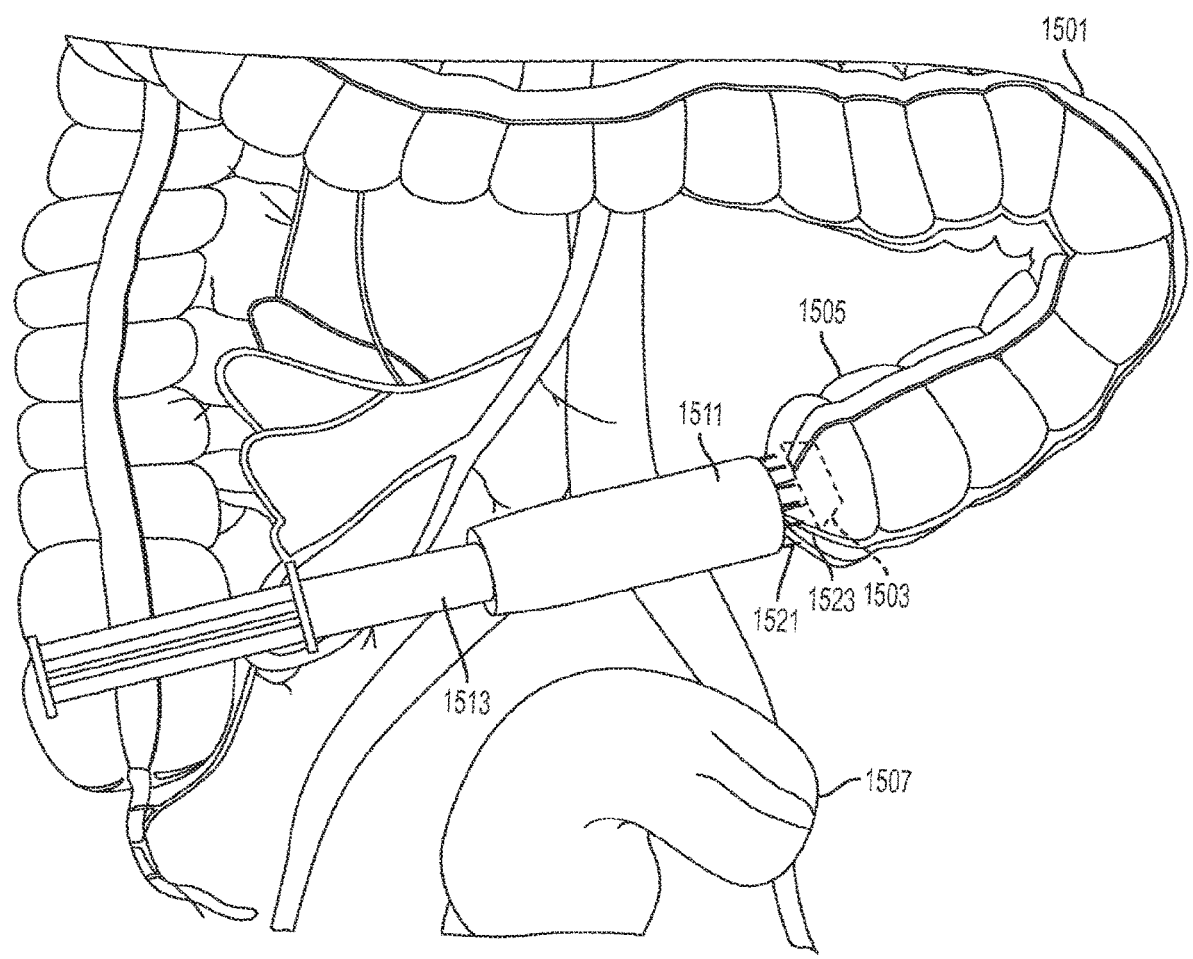
FIG. 15 shows a representative application of the injector and sensing anvil in colorectal resection procedure.

FIG. 15 shows a configuration of the present invention wherein the system is configured to assess oxygenation of a colorectal anastomosis. The colon 1501 is divided during surgery, and a sensing surgical stapler anvil 1503 (hidden from view inside the colon), such as described in FIG. 10*a* and FIG. 10*b* is inserted into the proximal end 1505 of the transected colon 1501. An injector 1511 (such as described in FIG. 14*a*, FIG. 4*b*, and FIG. 14*c*) injects oxygen-sensitive phosphorescent probe 1513 through needles 1521 into the colonic tissue 1523 of the site of the anastomosis at or near the proximal end 1505. The sensing anvil 1503 measures oxygenation at one or more points at the site of the anastomotic surface 1523. In one embodiment, the sensing anvil 1503 measures oxygenation with twelve banks of sensors interleaved between the staple forms configured for phosphorescent lifetime sensing. In a further embodiment, temperature sensors are also integrated into the sensing anvil 1503 for temperature compensation of the oxygenation measurements. As shown in FIG. 15, the distal end 1505 of the transected colon 1501 is left free, however an alternate configuration of the present invention can be adapted for injecting and sensing both the proximal 1505 and distal 1507 ends of colon 1501. FIG. 10 shows a representative procedure for lower anterior resection (LAR), but the present invention includes applications to all colorectal and coloanal resections, as well as other gastrointestinal procedures and other locations in the body.

In one embodiment, pressure sensors are incorporated into the sensing anvil 1503 to detect compression pressure of the tissue in the anastomosis 1523, and may further be used to standardize tissue compression pressure. In one method of use, the sensing anvil 1503 is activated to generate oxygenation maps of the anastomosis at various points in the procedure. In a representative example the sensing anvil can interrogate the proximal anastomotic tissue 1523 before creation of the anastomosis, during the approximation of the proximal 1523 and distal 1507 tissue, and immediately after firing the stapler, joining tissue and creating the anastomosis. This information may be used to guide the surgical procedure so as to affect a corrective action. Alternatively, the results may be used to classify the patient's risk of anastomotic failure and assist the operative team in the decision to fashion a temporary or permanent ostomy.

Figure 16A:
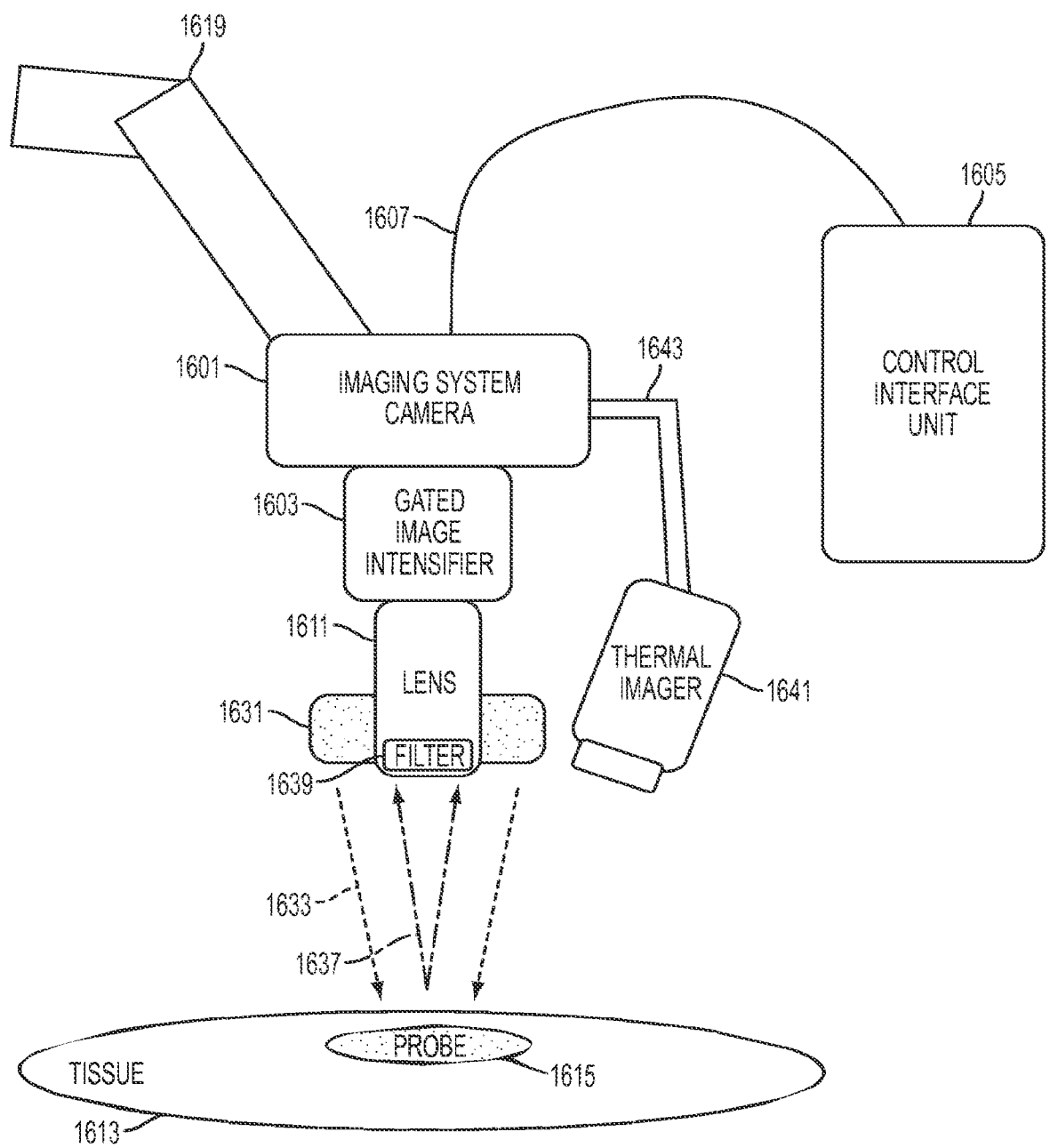
FIG. 16a shows a representative embodiment of an imaging system configured to assess fluorescent and or phosphorescent lifetime.

FIG. 16a shows a representative embodiment of an imaging system configured to assess fluorescent and or phosphorescent lifetime. In one embodiment, the system is configured to detect tissue oxygenation through phosphorescent lifetime imaging of an oxygen-sensitive probe injected into a tissue. In one configuration, the PLI system comprises a highly sensitive, low noise, high speed scientific camera 1601 coupled to a high speed gated image intensifier 1603; however in other embodiments lower cost traditional camera-based or other imaging systems may be utilized. The intensifier 1603 and the camera 1601 are coupled to an interface unit 1605, via coupling 1607, which controls the timing of the intensifier gating and the camera exposure, as well as streams images from the camera to a processor for analysis. In one embodiment, a computer is used for camera interfacing and image processing, and a computer-controlled data acquisition device provides timing control by acting as a dynamic delay generator (DDG). The intensifier 1603 and the camera 1601 may be separate components, or may be integrated into an intensified camera. Further, as described in FIG. 7a, FIG. 7b, and FIG. 7c, some or all of the functionality of the control interface unit 1605 may be combined into the camera. In one embodiment, a combined intensified camera comprises an FPGA or processor for preprocessing images, thus reducing the bandwidth requirements of connection 1607 to an external interface unit 1605.

The camera system comprises a lens 1611 to focus on a region of interest of the tissue, wherein the probe 1615 resides (either through local or system injection). In an overhead type system, the lens 1611 will focus on either an external tissue or a visible tissue in open surgery. The lens receives re-emitted light 1637 from the probe 1615 that was excited by excitation light 1633. The re-emitted light is selectively passed through filter 1639 to the lens 1611. In this configuration, the system may be attached to a mounting arm 1619 such as a ceiling mounted or floor mounted boom arm. The system may also be attached to a counterbalanced mounting arms similar to that of a surgical microscope, and further the head may have actuation so as to enable control of its position and alignment through robotic means. In an alternate configuration, the imaging system shown is a handheld unit configured to readily allow snap shots of tissue oxygenation similar to the use of a standard point and shoot camera.

The imaging system incorporates an illuminator light source 1631 to excite the probe 1615 in the tissue 1613. The illuminator 1631 light is modulated, and may be a pulsed light for time domain measurements or a sinusoidal excitation for frequency domain measurements. In one configuration, the illuminator 1631 contains a plethora of light emitters that form a circumferential ring around the optical axis of the camera lens 1611. The illumination light 1633 is focused into the same target region as the camera lens. In one embodiment, the illuminator contains multiple wavelengths of light emitters so as to provide excitation of the probe 1615 at multiple wavelengths or selectively excite multiple different probe types. Further, the illuminator 1631 may comprise both excitation light and visible light which are switched or multiplexed so as to enable clear visualization of the anatomy interleaved with oxygenation imaging. In another configuration, the illuminator may be an independent light source aimed at the target tissue and not necessarily aligned along the optical axis of the camera.

In one embodiment, the imaging system further comprises a means of assessing the temperature of the tissue containing the probe. Assessment of the subject tissue temperature, allows for temperature compensation of the temperature-dependent phosphorescent decay of the probe. The use of temperature measurements enables enhanced accuracy and robustness of absolute oxygen concentration measurements that are invariant to tissue temperature. Other physiologic and environmental factors may also be similarly measured to compensate for the lifetime to oxygen concentration calculation. In one embodiment, temperature is sensed at one or more discrete points through contact (e.g., thermocouple, RTD) or non-contact (e.g., optical) means. In one configuration, a thermal imager 1641 is coupled with the imaging system to create a temperature map of substantially the same region as the camera performing lifetime sensing. The thermal imaging camera 1641 may be rigidly coupled to the camera system 1601 via a mechanical coupler 1643. Registration may be performed to determine the correspondence between points in the lifetime image and the temperature map. This correspondence may be performed in real-time utilizing image-based registration techniques, or it may be performed a priori for a given configuration. One embodiment of the present invention incorporates a camera-based PLI system coupled with an infrared thermal imaging camera to detect both phosphorescent lifetime and temperature. Temperature and lifetime of a given pixel or region are both utilized in the determination of the corresponding oxygenation. In one approach, temperature is explicitly calculated and used directly with an a priori known temperature coefficient of the phosphorescent quenching process in calculating the conversion of phosphorescent lifetime to oxygenation. Thermal imager 1641 may incorporate polarizing or other filters to minimize/reduce infrared reflection.

The PLI system may comprise a laser or other alignment device affixed to a camera system 1601 and/or a light source 1631 to assist in directing the alignment to a desired field of view 1615. The alignment device may be one of a point source, cross hairs, and shaped to represent a region. The PLI system may also comprise an electromechanically actuated head in place of or coupled to arm 1619. The actuated head may be a robotic device. In one embodiment, the head is configured for dynamic tracking of a target or region of interest due to motion/misalignment.

The imaging system described in FIG. 16a may be used for a variety of applications. In one application, it is utilized for imaging gastrointestinal tissue such as colorectal tissue during colorectal cancer resection. It may be further used for assessing oxygenation and/or perfusion in tissue during organ transplants or vascular surgery. One use of the system is for assessing the viability of skin flaps by measuring their oxygenation. In one method of use, this system assesses the oxygenation of peripheral anatomy and utilizes the oxygenation to screen for peripheral vascular disease and/or guide interventions for peripheral vascular disease. The system of the method may be a boom-mounted imager, a handheld imaging instrument, or an alternate configuration. The system may generate individual images or multiple images over a specified time course at a specified repetition rate. The absolute tissue oxygenation and/or time-dependent variation in oxygenation may be presented.

Figure 16B:
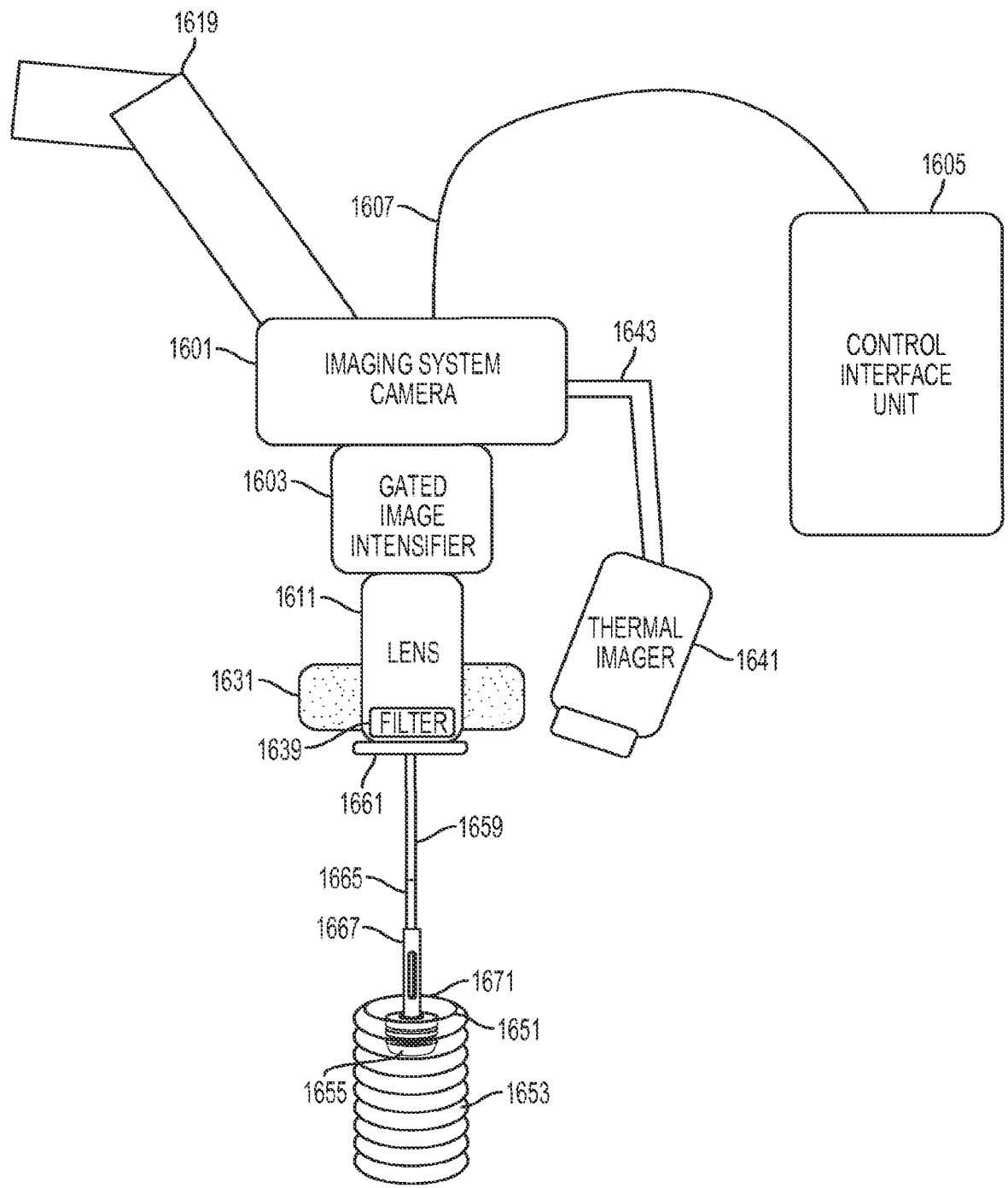
FIG. 16b shows a representative embodiment of an imaging system configured to assess fluorescent and or phosphorescent lifetime of tissue at the site of an anastomosis.

FIG. 16b shows a further representative embodiment of the imaging system described in FIG. 16a configured to assess fluorescent and or phosphorescent lifetime of tissue at the site of an anastomosis, specifically a colonic tissue anastomosis as previously described. The system can additionally be used to image other gastrointestinal anastomoses of other organs such as, but not limited to esophagus, stomach, and small intestine. In one configuration, the imaging system assesses the phosphorescent lifetime of an injected oxygen-sensitive probe. The probe 1651 is injected into colorectal tissue 1653 (typically the proximal end as described in FIG. 15) which has a surgical stapler anvil 1655 inserted into it in preparation for a surgical anastomosis. Anvil 1655 may be a traditional non-sensing anvil, or a sensing anvil as described in FIG. 10a and FIG. 10b. The probe 1651 is injected into the tissue 1653 utilizing an injector, such as that described in FIG. 14a, FIG. 15b, and FIG. 14c, or other means. The tissue in contact with the working surface (i.e. anvil's staple form surface) contains the probe and is directed towards the optical axis of the imaging system 1601. The imaging system further comprises an alignment guide 1659 that is coaxial with the optical axis of the camera 1601, intensifier 1603, and lens 1611. The alignment guide may be repeatably attached and removed from the lens 1611 via a quick-connect fitting 1661. A coupler 1655, which may be a quick-connect type connection, joins the alignment guide 1659 with the stalk 1667 of the surgical stapler anvil 1655. This system ensures that the proximal end of an anastomosis 1671 is fully imaged with the PLI system. In one embodiment, the PLI system further comprises a thermal imager 1641 to determine the temperature of the same tissue imaged by the PLI as described in FIG. 16b. The temperature may be used to compensate for the temperature-dependent phosphorescent lifetime in the conversion of lifetime to oxygen concentration. Temperature measurement may be performed via an imaging system of the target region, utilizing an injectable probe that aids in assessing temperature, contact measurement of the temperature, or other means.

In one method of use, the system in FIG. 16b generates an oxygen map of the proximal end of the anastomosis after resection and prior to joining with the distal end, and the information is used to guide the procedure. The guidance may incorporate corrective action such as additional dissection to reduce tension and improve blood supply. The system in FIG. 16a, which may be the same system as described in FIG. 16b with the alignment guide removed, may then be used for imaging the distal and/or proximal ends externally. The system may also be used in conjunction with a sensing anvil, such as that described in FIG. 10a and FIG. 10b.

The present invention includes, but is not limited to, sensing and mapping of tissue oxygenation based upon phosphorescent lifetime. This sensing technology may be used in conjunction with other technologies. The sensing technology associated with the invention may sense mechanical or biological properties. The sensing instruments may include one or more sensing modalities. The sensing modalities may include mechanical, optical, chemical, electrical, or other means for generating a signal indicative of a property of a subject tissue. In one embodiment, the sensing elements measure oxygenation through the use of a medium containing a phosphorescent probe or phosphor delivered into tissue. Other embodiments measure oxygenation through oximetry-based techniques. Further embodiments measure perfusion or flow rates through the time response of a fluorescent or phosphorescent medium introduced into the tissue.

Accordingly, one embodiment includes sensing surgical instruments and associated probes, injectors, processing, and visualization; the instruments capable of performing phosphorescent lifetime sensing at a plethora of discrete points, and using the phosphorescent lifetime measurements to generate temperature-compensated oxygen maps.

Another embodiment includes imaging systems and associated probes, injectors, processing, and visualization; the imaging systems capable of performing phosphorescent lifetime imaging of an array of points, and using the phosphorescent lifetime measurements to generate temperature-compensated oxygen maps; wherein, the oxygen maps are registered to endoscopic video images and used to identify suspect regions based on oxygenation measurements.

In an embodiment, the sensing components are incorporated into, or coupled to, a surgical instrument. Instruments may include traditional open, laparoscopic, endoscopic, bronchoscopic, otoscopic, opthalmoscopic, laryngoscopic, cystoscopic, colposcopic, intravascular, intraluminal, robotic, or other minimally invasive tools such as a purpose-built tissue interrogator or instrumented standard instrument such as a grasper, needle driver, stapler, clip applier, catheter, scissor, cautery, or retractor. Instruments may also include interrogators or other devices that may or may not be minimally invasive. In alternate embodiments, the sensing components are incorporated into a primary or secondary imaging system for endoscopy.

This imaging system may be used for diagnostic procedures, or for monitoring or guiding surgery. The technology may be incorporated into or associated with rigid or flexible endoscopy equipment. The technology may be further coupled with endoscopy equipment based upon light transmission through lenses or optical fibers, or it may be integrated with digital imaging systems with microcameras at the distal end. In a further embodiment, the imaging system disclosed in this invention may be a standalone camera-based system. This camera based system may be used for external monitoring of tissue (such as skin flaps), for internal imaging through either open surgical procedures or minimally invasive endoscopic procedures, for precision mapping of retinal oxygenation, used in conjunction with robotic surgery, or other means. As previously noted, this invention includes phosphorescent lifetime imaging of a phosphor with an oxygen-dependent quenching of phosphorescent response to an excitation. The invention also include sensing other physiologic parameters, sensing using other fluorescent or phosphorescent probes, measuring inherent fluorescent or phosphorescent response from tissue, or imaging an imaging agent or other biomarker or tag such as quantum dots. Optical sensing elements include but are not limited to light emitters including light emitting diodes (LEDs) and laser diodes, and light receivers including photodiodes (including avalanche photodiodes, photomultiplier tubes, silicon photomultipliers, and similar enhanced sensitivity detectors), photodiode arrays, CCD arrays (including enhanced sensitivity detectors such as electron multiplying EMCCDs), CMOS sensors, cameras, holographic imaging systems, image intensifiers (which may be coupled with or integrated into other detectors), and spectrometers.

The optical sensing elements are configured to measure at least one of tissue oxygenation, oxygen delivery, oxygen utilization, tissue characterization, and tissue general health using oximetry, phosphorescent techniques, or spectroscopic techniques, and at least one of tissue perfusion, tissue flow dynamics, tissue oxygen content, tissue chemical composition, tissue immunologic activity, tissue pathogen concentration, or tissue water content using fluorescence or phosphorescent based techniques. The fluorescence and phosphorescence based techniques include but are not limited to the following: monitoring and analyzing the intensity and time course of a fluorescent response responsive to the injection or activation of a fluorescent medium, determining oxygen quantities by measuring oxygen-dependent quenching of fluorescent or phosphorescent radiation using a sensitive material such as Ruthenium by both intensity and time resolved methods, determining oxygen concentration based on the quenching time response of injectable oxygen sensitive phosphorescent probes, and determining the target tissue property by quantitative fluorescent or phosphorescent methods including the use of quantum dots, or other biomarkers incorporating light re-emitting properties. In one configuration the device senses perfusion using Fluorescein, or IC Green, or other imaging agent. In one other configuration the device senses oxygen quenching of native tissue phosphorescence.

Included in this invention is a method for gating signal acquisition of a phosphorescent lifetime imaging system to physiologic parameters. Measurement of tissue oxygenation or other tissue characteristics can be measured in a gated fashion to standardize the measurement and allow for comparison. One representative example of the gated image acquisition is triggered with pulse and/or respiratory and/or peristaltic motion. Gated acquisition may also be based on measurements of peristalsis, respiratory motion, cardiac motion, cardiac output or pulsatile flow, EEG readings, EMG readings, motion sensors, or other inputs. A further method captures PLI measurements gated with at least one or respiration, cardiac output (i.e. pulse), peristalsis, or other internal or external motion. A further method provides for dynamically comparing PLI measurements at two or more time points in a physiologic cycle. One method determines the gate cycle from images acquired by the PLI system, and a further method provides for determining the cardiac cycle gate based off of images acquired of vasculature.

In one configuration of the present invention, the instrument is configured to sense oxygenation in multi-layered tissue, or to discriminate oxygenation at different depths of tissue. Using a phosphorescent oxygen sensing probe having multiple absorption wavelengths, the instrument can irradiate and excite a subset of the probe injected into tissue based on the excitation wavelength emitted from device since the penetration depth in tissue is wavelength-dependent. Oxygenation is discriminated at two or more depths or layers by exciting the tissue sequentially with multiple emission wavelengths at or near absorption peaks, and determining the corresponding quenching response. Sensing the deeper values will be a summation of multiple layers, oxygenation at deeper layers can be determined by accounting for the sensed oxygen at shallower layers. In an alternative approach, the phosphorescent decay of various oxygenation levels in heterogeneous luminescence systems (i.e. mixed oxygenations within the tissue sample) can be determined through deconvolution methods to produce a spectrum of oxygenation.

The present invention includes a medical imaging system, probes, and methods for assessment of phosphorescent or fluorescent lifetime of an injectable probe or natural auto fluorescence. In one configuration, at least one sensor is configured to obtain biological tissue oxygenation at a plethora of points utilizing the technique of oxygen dependent quenching of phosphorescence of an injectable probe. In another embodiment, the present invention measures lifetime of a marker or other probe in or on the body. In a further embodiment, lifetime of phosphorescence or fluorescence produced from native biologic tissue is assessed. Included in the present invention is a system and method for performing microinjection of a probe or imaging agent from tip of an endoscope or other instrument at one or more points; and a device for performing microinjection of a probe or imaging agent into tissue circumferentially at the working surface of a surgical stapler anvil.

The embodiments described above demonstrate how oxygen sensitive probes can be utilized with an imaging system for oxygen mapping of tissue. These embodiments are for meant as illustrative purposes. The described sensing configurations and approaches can be adapted to provide the described functionalities for other surgical instruments. Further, the techniques discussed should not be construed to be limited to use only with phosphorescent oxygen sensing probes.

The present invention can be practiced by employing conventional materials, methodology and equipment. Accordingly, the details of such materials, equipment and methodology are not set forth herein in detail. In the previous descriptions, numerous specific details are set forth, such as specific materials, structures, chemicals, processes, etc., in order to provide a thorough understanding of the present invention. However, it should be recognized that the present invention can be practiced without resorting to the details specifically set forth. In other instances, well known processing structures have not been described in detail, in order not to unnecessarily obscure the present invention.

Only exemplary embodiments of the present invention and but a few examples of its versatility are shown and described in the present disclosure. It is to be understood that the present invention is capable of use in various other combinations and environments and is capable of changes or modifications within the scope of the inventive concept as expressed herein.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

The invention claimed is:

1. An imaging system that resolves and maps a physiologic condition, or a proxy thereof, the imaging system comprising:
   an optical sensor configured for detection and measurement of lifetime of decay of light emitted by a medium, the medium comprising a first phosphorescent or fluorescent probe and a second phosphorescent or fluorescent probe, wherein either:
   (a) the first probe has a phosphorescent or fluorescent response that is oxygen-sensitive and the second probe has a phosphorescent or fluorescent response that is temperature-dependent and substantially oxygen-insensitive; or (b) the first probe and the second probe each have phosphorescent or fluorescent responses that are oxygen-dependent but the respective phosphorescent or fluorescent responses differ in (i) temperature dependence and (ii) excitation and/or emission wavelengths;

wherein said first and second probes have multiple absorption peaks; and the imaging system further comprising:

a light source configured to excite the medium sequentially at multiple emission wavelengths corresponding to the multiple absorption peaks of the first and second probes; and a processor configured to use the phosphorescent or fluorescent response of the second probe to compensate for temperature-dependent lifetime variation of the phosphorescent or fluorescent response of the first probe.

2. The imaging system of claim 1, wherein the imaging system comprises an endoscope.

3. The imaging system of claim 1, wherein the system is configured to register video images and oxygenation maps, and further the system is configured to display the video images with an overlay of said oxygenation maps.

4. The imaging system of claim 1, wherein at least one of the first probe and the second probe are injectable.

5. The imaging system of claim 1, wherein the physiological condition is oxygenation of a tissue.

6. The imaging system of claim 5, wherein the processor is configured to compensate for the temperature-dependent lifetime variation of the phosphorescent or fluorescent response of the first probe in order to resolve the oxygenation.

7. The imaging system of claim 1, wherein the processor is configured to generate a map of lifetime of decay from the detected lifetime of the decay in an optical sensor field of view, the map of lifetime of decay comprising measurements of a plurality of points.

8. The imaging system of claim 7, wherein the processor is configured to generate a temperature map from detected temperature, the temperature map comprising measurements of a plurality of points.

9. The imaging system of claim 8, wherein the processor is configured to:

generate a map of the physiologic condition or the proxy thereof by solving a temperature-dependent relationship between the map of lifetime of decay and the physiologic condition or the proxy thereof using the temperature map; and transmit the generated map of the physiologic condition or the proxy thereof to a display.

10. The imaging system of claim 1, wherein the medium comprises a tissue.

11. The imaging system of claim 1, wherein the medium comprises an injectable molecular probe.

12. The imaging system of claim 11, wherein calibration parameters of the molecular probe comprise a quenching constant (kq) and a phosphorescence lifetime in an absence of oxygen ($\tau 0$).

* * * * *